US012677146B2

(12) United States Patent
Xu et al.

(10) Patent No.: US 12,677,146 B2
(45) Date of Patent: Jul. 7, 2026

(54) METHOD AND SYSTEM FOR NON-CONTACT MOTION-BASED USER AUTHENTICATION

(71) Applicants: The Research Foundation for The State University of New York, Amherst, NY (US); Texas Tech University System, Lubbock, TX (US)

(72) Inventors: Wenyao Xu, Buffalo, NY (US); Changzhi Li, Lubbock, TX (US)

(73) Assignee: The Research Foundation for The State University of New York, Amherst, NY (US)

( * ) Notice: Subject to any disclaimer, the term of this patent is extended or adjusted under 35 U.S.C. 154(b) by 127 days.

(21) Appl. No.: 16/572,588

(22) Filed: Sep. 16, 2019

(65) Prior Publication Data
US 2020/0236545 A1 Jul. 23, 2020

Related U.S. Application Data

(60) Provisional application No. 62/731,792, filed on Sep. 14, 2018.

(51) Int. Cl.
 *H04W 12/06* (2021.01)
 *A61B 5/11* (2006.01)
 (Continued)

(52) U.S. Cl.
 CPC ........... *H04W 12/06* (2013.01); *A61B 5/1102* (2013.01); *A61B 5/117* (2013.01); *G01S 7/35* (2013.01);
 (Continued)

(58) Field of Classification Search
 CPC ....... H04W 12/06; G16H 40/67; G16H 50/30; A61B 5/1102; A61B 5/117; G01S 7/35; G01S 7/415; G06Q 50/265
 See application file for complete search history.

(56) References Cited

U.S. PATENT DOCUMENTS 4,852,578 A * 8/1989 Companion ............. A61B 8/08
 600/449
5,058,591 A * 10/1991 Companion ......... A61B 8/0858
 600/449
(Continued)

FOREIGN PATENT DOCUMENTS

EP 3437554 A1 2/2019
WO WO 2007010460 * 1/2007
(Continued)

OTHER PUBLICATIONS

Paiva et al., Beat-ID Towards a computationally low-cost single heartbeat biometric identity check system based on electrocardiogram wave morphology (Year: 2017).*

(Continued)

*Primary Examiner* — Quang Pham
(74) *Attorney, Agent, or Firm* — Hodgson Russ LLP

(57) ABSTRACT

Methods and systems are provided for authenticating an individual using a motion of a physiological structure. For example, an individual may be authenticated using their cardiac motion. A first radiofrequency ("RF") signal is transmitted towards the physiological structure of the individual. A first RF return signal is received, where the first RF return signal corresponds to the transmitted first RF signal. The first RF signal and first RF return signal are processed to obtain a motion signal. One or more values are determined for each fiducial point of a set of pre-determined fiducial points in the motion signal. The set of pre-determined fiducial points corresponds to physical movements of the physiological structure. The individual is authenticated based on the values of one or more fiducial points.

9 Claims, 10 Drawing Sheets

(51) Int. Cl.

| | |
|---|---|
| *A61B 5/117* | (2016.01) |
| *G01S 7/35* | (2006.01) |
| *G01S 7/41* | (2006.01) |
| *G06Q 50/26* | (2012.01) |
| *G16H 40/67* | (2018.01) |
| *G16H 50/30* | (2018.01) |

(52) U.S. Cl.
CPC ............ *G01S 7/415* (2013.01); *G06Q 50/265* (2013.01); *G16H 40/67* (2018.01); *G16H 50/30* (2018.01)

(56) References Cited

U.S. PATENT DOCUMENTS

| | | | | |
|---|---|---|---|---|
| 6,621,278 | B2 * | 9/2003 | Ariav ................... | A61B 5/0507 600/407 |
| 6,783,498 | B2 | 8/2004 | Sackner et al. | |
| 7,889,053 | B2 * | 2/2011 | McGrath ................. | G07C 9/37 340/5.1 |
| 8,554,311 | B2 * | 10/2013 | Warner ................... | A61B 5/318 600/509 |
| 9,026,193 | B2 * | 5/2015 | Pahlevan ........... | A61B 5/02438 600/407 |
| 9,396,643 | B2 | 7/2016 | He et al. | |
| 9,408,549 | B2 | 8/2016 | Brockway et al. | |
| 9,558,336 | B2 | 1/2017 | Lee | |
| 9,585,577 | B2 | 3/2017 | Banet et al. | |
| 9,687,159 | B2 * | 6/2017 | Ochs .................... | A61B 5/7239 |
| 9,770,212 | B2 * | 9/2017 | Shan .................... | A61B 5/0816 |
| 10,426,411 | B2 * | 10/2019 | Li ........................ | A61B 5/1102 |
| 2003/0135097 | A1 * | 7/2003 | Wiederhold ............. | G06K 9/00 600/509 |
| 2005/0234355 | A1 * | 10/2005 | Rowlandson ............ | A61B 6/56 600/509 |
| 2006/0122525 | A1 * | 6/2006 | Shusterman ........... | A61B 5/411 600/513 |
| 2007/0060799 | A1 * | 3/2007 | Lyon ...................... | A61B 34/10 382/128 |
| 2007/0167758 | A1 | 7/2007 | Costello | |
| 2008/0077015 | A1 | 3/2008 | Boric-Lubecke et al. | |
| 2008/0177280 | A1 * | 7/2008 | Adler ...................... | A61B 90/10 901/41 |
| 2008/0234594 | A1 * | 9/2008 | Brooks .................... | A61B 7/04 600/513 |
| 2009/0299203 | A1 * | 12/2009 | De Voir ................. | A61B 5/053 600/509 |
| 2010/0152600 | A1 | 6/2010 | Droitcour et al. | |
| 2010/0204599 | A1 * | 8/2010 | Pu .......................... | A61B 5/349 600/523 |
| 2011/0021928 | A1 | 1/2011 | Giovangrandi et al. | |
| 2011/0282227 | A1 * | 11/2011 | Zhang .................... | A61B 5/349 600/516 |
| 2013/0053653 | A1 * | 2/2013 | Cuddihy .............. | A61B 5/0816 600/301 |
| 2013/0079606 | A1 * | 3/2013 | McGonigle ........ | A61B 5/14551 600/323 |
| 2013/0237868 | A1 * | 9/2013 | Choi ...................... | A61B 5/352 600/509 |
| 2013/0243105 | A1 * | 9/2013 | Lei ...................... | H04L 67/5651 375/241 |
| 2014/0188770 | A1 * | 7/2014 | Agrafioti ............... | G06F 21/316 706/13 |
| 2014/0364756 | A1 * | 12/2014 | Brockway .............. | A61B 5/316 600/513 |
| 2015/0094558 | A1 * | 4/2015 | Russell .................. | A61B 5/282 600/386 |
| 2015/0157239 | A1 | 6/2015 | Rissacher et al. | |
| 2015/0359463 | A1 * | 12/2015 | Matthews .............. | A61B 5/024 600/407 |

| | | | | |
|---|---|---|---|---|
| 2016/0063233 | A1 * | 3/2016 | Bae ........................ | A61B 5/352 726/19 |
| 2016/0235318 | A1 * | 8/2016 | Sarkar .................... | A61B 5/361 |
| 2017/0014093 | A1 * | 1/2017 | Hosoki ............... | A61B 6/5217 |
| 2018/0008829 | A1 * | 1/2018 | An ...................... | A61N 1/36535 |
| 2018/0049669 | A1 * | 2/2018 | Vu ........................ | A61B 5/0816 |
| 2018/0106897 | A1 | 4/2018 | Shouldice et al. | |
| 2018/0239873 | A1 * | 8/2018 | Eda ........................ | G16H 70/60 |
| 2018/0317779 | A1 * | 11/2018 | Gregg .................. | A61B 5/1127 |
| 2019/0050863 | A1 * | 2/2019 | Agrawal .......... | G06Q 20/40145 |
| 2019/0076096 | A1 | 3/2019 | Lin et al. | |
| 2019/0212436 | A1 * | 7/2019 | Baheti ...................... | G01S 13/88 |
| 2020/0022607 | A1 * | 1/2020 | Pratt .................... | A61B 5/0803 |
| 2020/0121214 | A1 * | 4/2020 | Hyde ....................... | A61B 7/04 |
| 2020/0121215 | A1 * | 4/2020 | Hyde ....................... | G01S 7/40 |
| 2022/0192574 | A1 * | 6/2022 | Vennelaganti ......... | G16H 40/67 |

FOREIGN PATENT DOCUMENTS

| | | | | |
|---|---|---|---|---|
| WO | WO-2008102291 A2 * | 8/2008 | ........... | A61B 5/0507 |
| WO | 2018050913 A1 | 3/2018 | | |
| WO | 2019122412 A1 | 6/2019 | | |
| WO | 2019122413 A1 | 6/2019 | | |
| WO | 2019122414 A1 | 6/2019 | | |

OTHER PUBLICATIONS

Li et al., Random Body Movement Cancellation in Doppler Radar Vital Sign Detection (Year: 2009).*

Rahman et al., DoppleSleep a Contactless Unobtrusive Sleep Sensing System Using Short-Range Doppler Radar (Year: 2015).*

Ren et al., Phase-Based Methods for Heart Rate Detection Using UWB Impulse Doppler Radar (Year: 2016).*

Zhao et al., TrueHeart Continuous Authentication on Wrist-worn Wearables Using PPG-based Biometrics (Year: 2020).*

Xia et al., The Delineation of Fiducial Points for Non-Contact Radar Seismocardiogram Signals without Concurrent ECG (Year: 2021).*

Lin et al., Cardiac Scan a Non-contact and Continuous Heart-based User Authentication System (Year: 2017).*

Mitchell et al., Electrocardiogram-based biometrics for user identifcaiotn using your heartbeat as a digital key, (Year: 2023).*

Xia et al., Non-Contact_Sensing_of_Seismocardiogram_Signals_Using_Microwave_Doppler_Radar (Year: 2018).*

Tech Briefs, Authentication by Heart Radars New Role in Biometrics (Year: 2015).*

Chen Song, Feng Lin, Yan Zhuang, Wenyao Xu, Changzhi Li, Kui Ren, Cardiac Scan: A Non-Contact and Continuous Heart-Based User Authentication System, MobiCom '17: Proceedings of the 23rd Annual International Conference on Mobile Computing and Networking, Oct. 16, 2017, pp. 315-328.

Qiancheng Liang, Lisheng Xu, Nan Bao, Lin Qi, Jingjing Shi, Yicheng Yang, Yudong Yao, Research on Non-Contact Monitoring System for Human Physiological Signal and Body Movement, Biosensors, Apr. 19, 2019, pp. 1-13, 9:58.

Peibei Cao, Weijie Xia, Yi Li, Heart ID: Human Identification Based on Radar Micro-Doppler Signatures of the Heart Using Deep Learning, Remote Sensing, May 23, 2019, pp. 1-16, 11:1220.

Syed W. Shah, Salil S. Kanhere, Smart user identification using cardiopulmonary activity, Pervasive and Mobile Computing 58, May 22, 2019, pp. 1-20.

Mei Chen, Joseph A. O'sullivan, Naveen Singla, Erik J. Sirevaag, Sean D. Kristjansson, Po-Hsiang Lai, Alan D. Kaplan, and John W. Rohrbaugh, Laser Doppler Vibrometry Measures of Physiological Function: Evaluation of Biometric Capabilities, IEEE Transactions on Information Forensics and Security, Sep. 1, 2010, pp. 449-460, vol. 5, No. 3.

Dan Rissacher, Dan Galy, Cardiac Radar for Biometric Identification using Nearest Neighbour of Continuous Wavelet Transform Peaks, IEEE International Conference on Identity, Security and Behavior Analysis (ISBA 2015), Mar. 23, 2015, pp. 1-6.

* cited by examiner

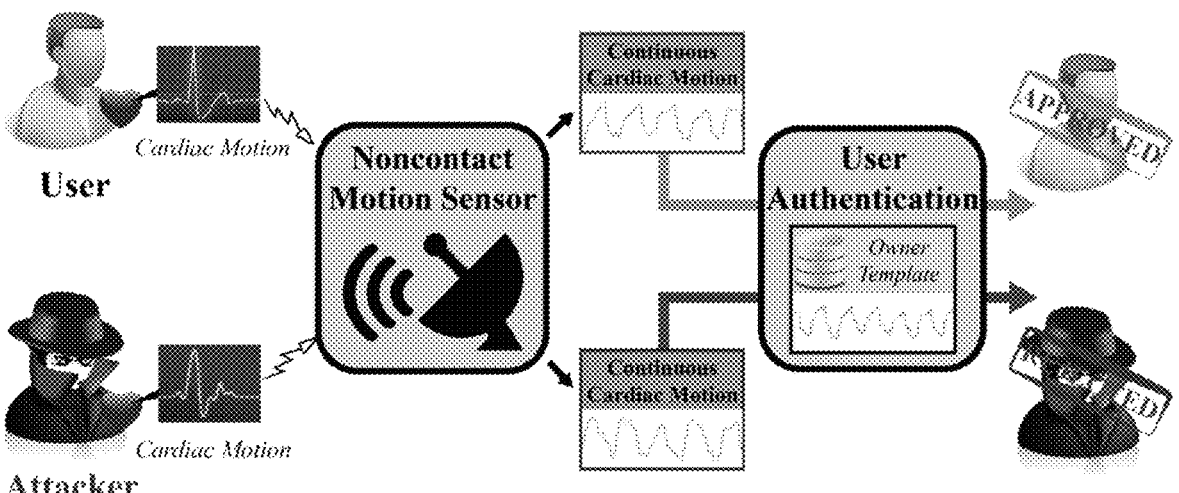
Fig. 1
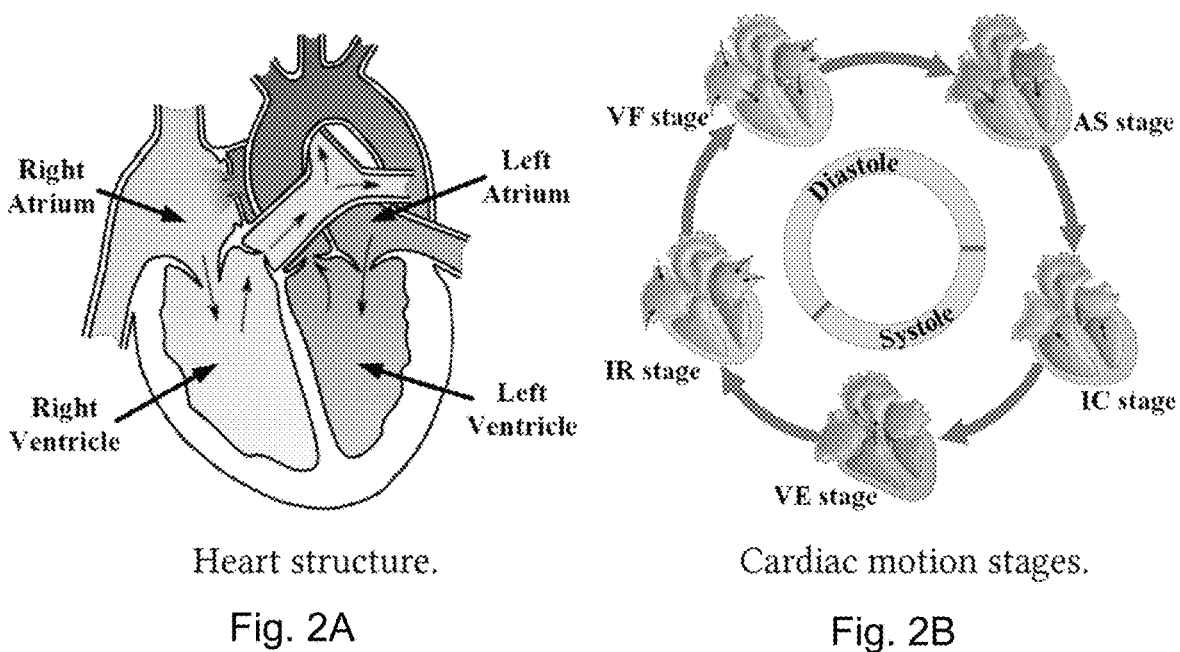
Heart structure.                    Cardiac motion stages.
Fig. 2A                             Fig. 2B $$\delta = \frac{|\vec{a} \times \vec{c}|}{|\vec{a}|}$$

(a)         (b)         (c)

METHOD AND SYSTEM FOR NON-CONTACT MOTION-BASED USER AUTHENTICATION

CROSS-REFERENCE TO RELATED APPLICATIONS

This application claims priority to U.S. Provisional Application No. 62/731,792, filed on Sep. 14, 2018, the disclosure of which is incorporated herein by reference.

STATEMENT REGARDING FEDERALLY SPONSORED RESEARCH

This invention was made with government support under contract no. 1718375 awarded by the National Science Foundation. The government has certain rights in the invention.

FIELD OF THE DISCLOSURE

The present disclosure relates to authentication methods, and more particularly to biometric-based authentication methods.

BACKGROUND OF THE DISCLOSURE

Continuous authentication improves upon one-pass validation by continuously verifying over the lifetime of a session that the system is operated by the same user as at initial login. It can prevent access by adversaries when the legitimate user is away or overwhelmed. Governments and private companies increasingly demand more secure authentication, because of credential compromises due to weak cryptographic mechanisms (hacking, password theft, etc.) and user carelessness. In 2014 alone, more than one billion personal records were illegally accessed including, health, financial, email and home address data, and other personal information like social security numbers.

Existing solutions for continuous authentication have certain limitations. Specifically, traditional methods demand the user to intentionally engage with the authentication system, such as scan a fingerprint or enter in a password after a certain period. Regardless of the vulnerability, these methods impact usability in practice. Several studies also have proposed advanced continuous authentication mechanisms based on the user's behavioral biometrics, such as keystroke dynamics and gaze pattern. However, keystroke dynamics require the user to keep typing on the keyboard, while gaze patterns require the user to face and continuously look at the screen. Other methods, such as continuous face recognition on Windows 10 Hello, are also reported to be vulnerable to spoofing or replay attacks. Recently, the physiological biometrics-based approaches are emerging for continuous authentication, such as pulse response, however, they all require the human body to make contact with certain devices.

In recent years, there has been increased interest in radio-based (e.g., Wi-Fi) human sensing applications. However, little work exists for radio-based identification of individuals. Accordingly, there continues to be a long-felt need for non-contact techniques to identify individuals in a manner that may be used continuously.

BRIEF SUMMARY OF THE DISCLOSURE

The present disclosure provides a trustworthy, continuous, and non-contact user authentication approach based on a physiological movement (e.g., heart-related) biometric that works in a daily-life environment. In some embodiments, a continuous authentication system, named Cardiac Scan, is based on geometric and non-volitional features of cardiac motion. Cardiac motion is an automatic heart deformation caused by self-excitement of the cardiac muscle, which is unique to each user and is difficult (if not impossible) to counterfeit. Cardiac Scan can measure the unique cardiac motion of individuals with regard to the cardiac moving dynamics (e.g., speed, acceleration, etc.) and heart-blood circulation functionality in individuals. Cardiac Scan features intrinsic liveness detection, unobtrusiveness, cost-effectiveness, and high usability. Some embodiments provide a high-resolution cardiac motion sensing system utilizing a smart DC-coupled continuous-wave radar. Fiducial-based invariant identity descriptors of cardiac motion are extracted after the radar signal demodulation. A pilot study was conducted with 78 subjects to evaluate Cardiac Scan in accuracy, authentication time, permanence, evaluation in complex conditions, and vulnerability. In the study, Cardiac Scan achieved 98.61% balanced accuracy (BAC) and 4.42% equal error rate (EER) in a real-world setup. We demonstrate that Cardiac Scan is a robust and usable continuous authentication system.

DESCRIPTION OF THE DRAWINGS

For a fuller understanding of the nature and objects of the disclosure, reference should be made to the following detailed description taken in conjunction with the accompanying drawings, in which:

FIG. 1: A continuous authentication method using cardiac motion captured by a non-contact radar according to an embodiment of the present disclosure.

FIGS. 2A & 2B: Heart structure and dynamics.

DETAILED DESCRIPTION OF THE DISCLOSURE

Embodiments of the present disclosure (some embodiments are referred to herein as "Cardiac Scan") provide a secure and trustworthy continuous user authentication scheme via non-contact cardiac motion sensing. The present disclosure is illustrated in the following exemplary embodiments and further described below under the heading "Further Discussion."

FIG. 1 shows a diagram depicting a working paradigm of Cardiac Scan. The authentic user's credential is stored in a database prior to authentication, a new incoming physiological motion (such as, for example, a heart (cardiac) motion) may be matched to the stored credential to make a decision as to whether the access request is from an authorized user or a malicious adversary. For convenience, descriptions of the present disclosure describe non-limiting embodiments utilizing cardiac motion. One having skill will recognize that the techniques may be extended to other physiological motion(s), which are included within the cope of the disclosure.

As a live individual trait, a heart-based biometric is unique (i.e., distinguishable across subjects), measurable (i.e., hard to hide), non-volitional (i.e., unknown to the user), secure (i.e., difficult to counterfeit), and present in all living individuals (i.e., intrinsic liveness). The present disclosure provides a cardiac-motion-based continuous authentication scheme in a non-contact way. Different from electrocardiogram (ECG), the presently disclosed technique utilizes cardiac motion, which is a heart-based functional behavior determined by the intrinsic geometric structure of the heart. Specifically, there are at least three challenges involved: (1) how to obtain the high-resolution cardiac motion information unobtrusively; (2) how to extract invariant geometric-based features for each heart with regard to the cardiac motion mechanism; and (3) how to examine the usability and security of the continuous authentication scheme.

Work related to the present disclosure focused on several corresponding areas: (1) development of a smart DC-coupled continuous-wave (CW) Doppler radar sensor to continuously capture high-resolution cardiac motion information from a distance; (2) identifying fiducial descriptors of cardiac motion based on the heart geometric characteristics; (3) conducting intensive evaluations (e.g., accuracy performance, usability, and complex use conditions) to validate performance and examine security against replay attacks. Through a pilot study with 78 subjects, an embodiment of Cardiac Scan achieved 98.61% balanced accuracy (BAC) and 4.42% equal error rate (EER). All these studies demonstrate that Cardiac Scan is a robust and usable continuous authentication system. Moreover, Cardiac Scan can be conveniently integrated with existing one-pass user verification techniques (e.g., personal identification number (PIN), fingerprint, iris scan, and face) to enhance the continuous authentication capability of existing systems.

Figure 18:
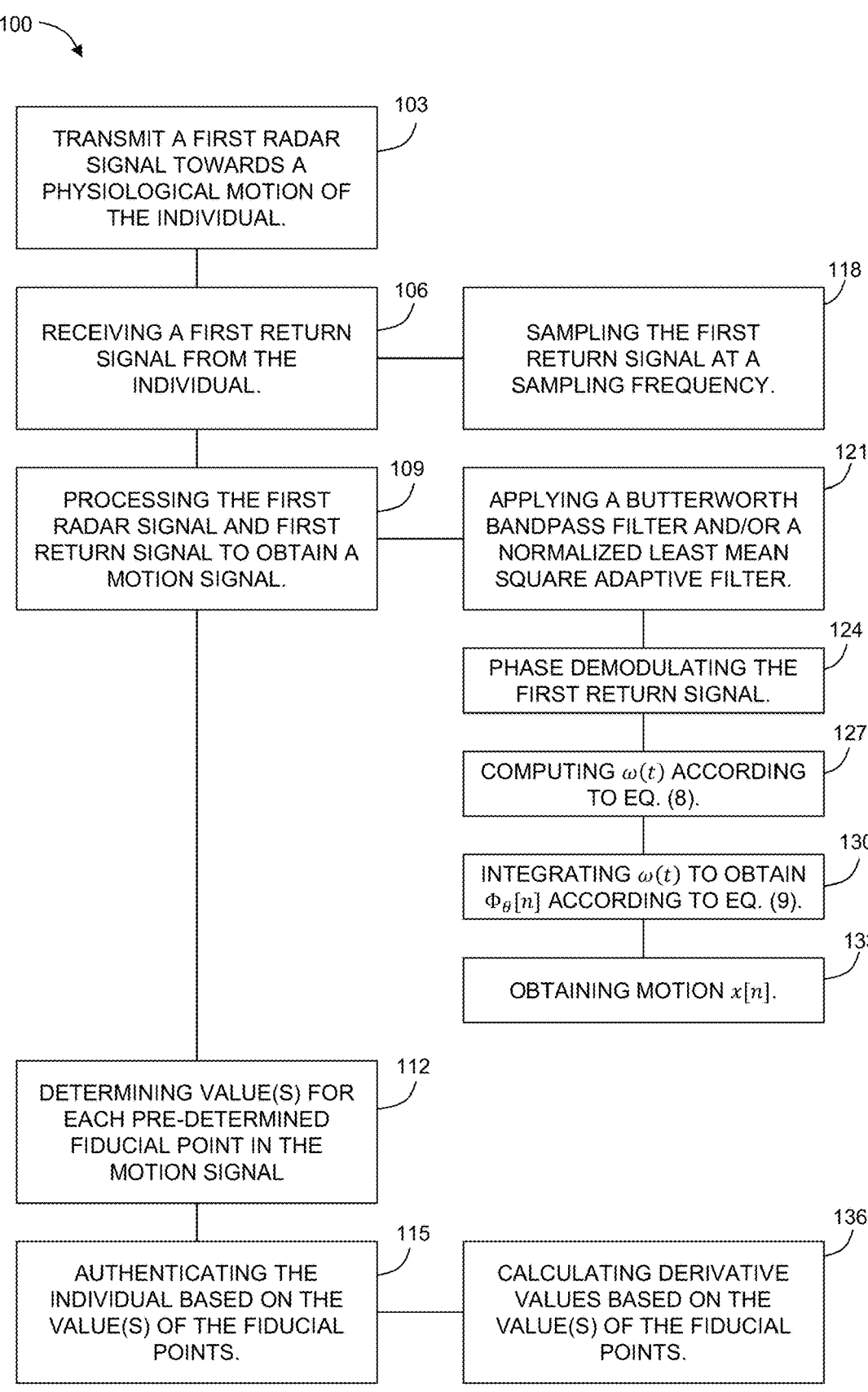
FIG. 18: A chart according to another embodiment of the present disclosure.

In a first aspect, the present disclosure may be embodied as a method 100 for authenticating an individual using a motion of a physiological structure (i.e., a physiological motion) (see, e.g., FIG. 18). For example, the physiological structure may be a heart, and the individual may be authenticated based on cardiac motion. A first RF signal is transmitted 103 toward the subject physiological structure of the individual. As further described below, the first RF signal is be a radar signal such as, for example, a Doppler radar. The first RF signal may have a frequency of 2.4 GHz to 40 GHz, though the frequency may be higher or lower as may be appropriate for a particular application. A first RF return signal is received 106. The received 106 first RF return signal corresponds to the transmitted 103 first RF signal interacting with the physiological motion. In some embodiments, the first RF return signal is received 106 by sampling 118 the first RF return signal at a sampling frequency. The sampling frequency may be 60 Hz to 500 Hz, or higher or lower as may be appropriate for a particular application.

The first RF signal and/or the first RF return signal are processed 109 to obtain a motion signal. Processing 109 may occur using a processor, circuits having discrete components, or any other techniques and/or structures used to process such electronic signals as are known, or combinations thereof. In some embodiments, the step of processing 109 the signals includes applying 121 a Butterworth bandpass filter and/or a normalized least mean square adaptive filter to reduce noise. Such one-pass noise reduction techniques may be considered pre-processing for the purposes of reducing noise levels.

In some embodiments, processing 109 includes phase demodulating the first RF return signal as further described below. For example, the first RF return signal may be demodulated 124 using an arctangent demodulation. A derivative to the arctangent-demodulated phase information may be calculated 127 as $\omega(t)$ (see, e.g., Equation (8) below). $\omega(t)$ may then be integrated 130 to obtain signal phase $\Phi_\theta[n]$. And the physiological motion signal may then be obtained 133 based on the signal phase $\Phi_\theta[n]$. Each of these steps is further described below under the heading "Radio Signal Processing Schemes."

A pre-determined set of fiducial points corresponds to physical movements of the physiological structure as further described below under the heading "Heart Geometric Features." The method 100 may include determining 112 one or more values for each fiducial point of the set of fiducial points. In the exemplary case of cardiac motion, the values of fiducial points may correspond to, for example, the amplitude of one or more fiducial points (e.g., with respect to the amplitude(s) of one or more other fiducial points) or the time of one or more fiducial points (e.g., relative time with respect to a cycle of the cardiac motion signal). For example, the one or more values for each fiducial point correspond to the amplitude difference and/or time difference between one or more fiducial point pairs. The individual is authenticated 115 based on the determined 112 one or more values of the fiducial points. In some embodiments, derivative values may be calculated 136 based on the value(s) of the fiducial points.

Figure 19:
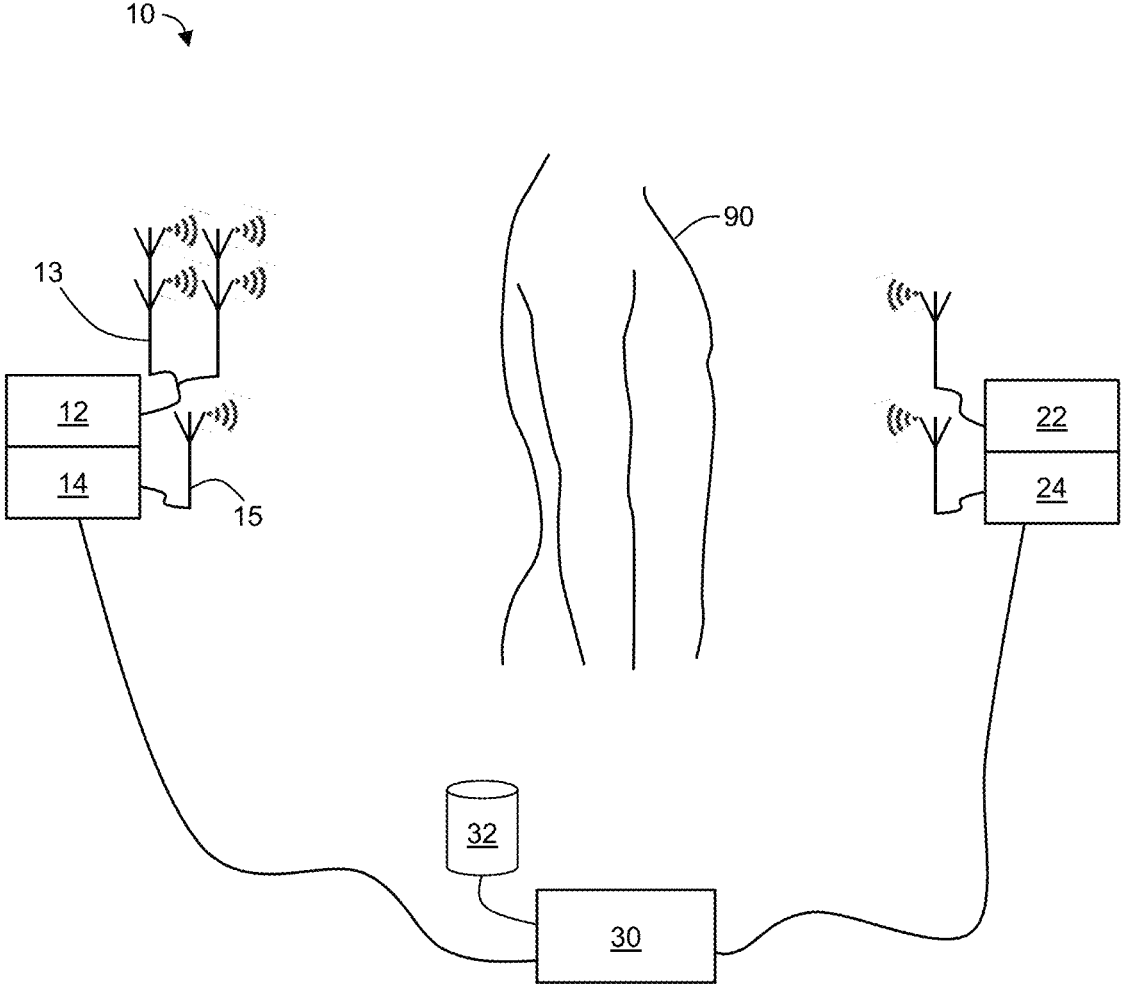
FIG. 19: A diagram depicting a system according to another embodiment of the present disclosure.

In another aspect, the present disclosure may be embodied as an authentication system 10 (see, e.g., FIG. 19). A first radar transmitter 12 is configured to emit a first RF signal towards a physiological motion of an individual. A first radar receiver 14 is configured to receive a corresponding first RF return signal modulated by the physiological motion of the individual. In some embodiments, the first radar transmitter 12 and the first radar receiver 14 make up a portion of a radar sensor, such as, for example, a continuous wave, DC-coupled radar sensor. The radar components may operate at a frequency selected from within the range of, for example, 2.4 GHz to 40 GHz, inclusive. The radar transmitter 12 and receiver 14 may each include an antenna 13,15. The transmitter 12 may be configured with a beam controller. For example, the transmitter may include a multi-element antenna for beam steering such as, for example, a phased array antenna.

The first radar transmitter 12 may be configured to provide the first RF signal to a multi-element antenna 13. The beam controller may be configured to simultaneously adjust a phase and an amplitude of the first RF signal provided to two or more elements of an antenna 13. In some embodiments, the beam controller is configured to adjust the phase and amplitude of the first RF signal in the complex domain. In some embodiments, the beam controller further comprises a vector multiplier. The vector multiplier may be configured to split the first RF signal into an in-phase component and an out-of-phase component; amplify each of the in-phase component and out-of-phase component; and add the amplified in- and out-of-phase components together to yield a complex modulation of the transmit carrier signal.

The system 10 further includes a processor 30 configured to process the first RF signal and/or the first RF return signal to yield a user profile of the individual 90 based on the physiological motion. The processor 30 is further configured to validate the user profile against one or more stored user profiles to authenticate the individual.

The processor 30 may be in communication with and/or include a memory. The memory 32 may store data such as, for example, user profiles. The memory can be, for example, a Random-Access Memory (RAM) (e.g., a dynamic RAM, a static RAM), a flash memory, a removable memory, and/or so forth. In some instances, instructions associated with performing the operations described herein (e.g., determine a user profile of an individual based on the first RF signal and first RF return signal, validate the user profile against one or more stored user profiles) can be stored within the memory and/or a storage medium (which, in some embodiments, includes a database in which the instructions are stored) and the instructions are executed at the processor.

In some instances, the processor includes one or more modules and/or components. Each module/component executed by the processor can be any combination of hardware-based module/component (e.g., a field-programmable gate array (FPGA), an application specific integrated circuit (ASIC), a digital signal processor (DSP), one or more circuits made up of discrete components, combinations of such modules/components, etc.), software-based module (e.g., a module of computer code stored in the memory and/or in the database, and/or executed at the processor, combinations, etc.), and/or a combination of hardware- and software-based modules. Each module/component executed by the processor is capable of performing one or more specific functions/operations as described herein. In some instances, the modules/components included and executed in the processor can be, for example, a process, application, virtual machine, and/or some other hardware or software module/component. The processor can be any suitable processor configured to run and/or execute those modules/components. The processor can be any suitable processing device configured to run and/or execute a set of instructions or code. For example, the processor can be a general purpose processor, a central processing unit (CPU), an accelerated processing unit (APU), a field-programmable gate array (FPGA), an application specific integrated circuit (ASIC), a digital signal processor (DSP), and/or the like.

Some instances described herein relate to a computer storage product with a non-transitory computer-readable medium (also can be referred to as a non-transitory processor readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other instances described herein relate to a computer program product, which can include, for example, the instructions and/or computer code discussed herein.

Examples of computer code include, but are not limited to, micro-code or microinstructions, machine instructions, such as produced by a compiler, code used to produce a web service, and files containing higher-level instructions that are executed by a computer using an interpreter. For example, instances may be implemented using Java, C++, .NET, or other programming languages (e.g., object-oriented programming languages) and development tools. Additional examples of computer code include, but are not limited to, control signals, encrypted code, and compressed code.

Some embodiments of the authentication system include a second radar transmitter 22 configured to emit a second RF signal toward the physiological motion (i.e., the physiological structure of the individual 90). In some embodiments, the second RF signal is transmitted in a direction opposite a direction of the first RF signal. A second radar receiver 24 may be configured to receive a second RF return signal corresponding to the second RF signal modulated by the physiological motion. As such, the processor 30 may be further configured to process the first RF return signal and the second RF return signal to suppress interference from body movement (as further described below).

The authentication system may further include a radio frequency coarse-tuning circuit configured to add a portion of the first RF signal to the first RF return signal. The authentication system may further include a baseband fine-tuning circuit configured to dynamically adjust an amplifier bias to a level maximizing dynamic range.

The authentication system may further include a secured device. The secured device may be a mobile device such as, for example, a computer, a phone, a personal digital assistance, or a tablet. The secured device is in communication with the processor such that an authenticated individual is permitted access to the secured device (i.e., the secured device is "unlocked" so as to allow use of the secured device). The secured device may have one or more integrated one-pass user techniques such as, for example, personal identification number (PIN), fingerprint, iris scan, and face scan, and the like.

FURTHER DISCUSSION

Design Goals

The design of the Cardiac Scan system takes into account several design goals, including the following.

Intrinsic Liveness: An aspect of a biometric system is intrinsic liveness detection, i.e., the ability to distinguish if the authentication sample is a "live" user or a replay attack. Cardiac motion exists only in a "live" user and represents heart deformation when the heart is in contraction and relaxation states.

Unobtrusive Authentication: The authentication system may identify an authentic user in an unobtrusive way so that the user has no obligation to change his/her behavior to adapt to the system. Continuous authentication further is further benefited where the authentication process is unobtrusive so that the user does not need to interrupt current work to authenticate. Cardiac Scan can perform unobtrusive authentication through a human-safe radio signal.

Highly Secure: The biometric should be highly secure and unique, making it difficult to be forged and stolen. Cardiac Scan measures live cardiac motion, which relates to the cardiac muscle structure of the user and therefore is impossible to completely mimic.

Cost-effective and Easy-to-Use: Some biometrics seem to have reliable and robust features, but information acquisition for the biometrics require expensive devices and specific conditions, such as an iris/retina authentication system. Cardiac Scan can be implemented using low-cost off-the-shelf components to build the radar sensor and is easy to use at a distance because of the propagation of the radio signal.

Resilient to Background Noise and Use Conditions: The biometric system should also be resilient to background noise and use conditions, no matter what the surrounding environmental conditions are. Camera-based systems, including face and iris recognition, usually have deteriorated performance with either too strong or too weak illuminations. Cardiac Scan uses a radio signal that is robust to environmental change and can penetrate through obstacles to accurately sense cardiac movement. Also, due to sensing utilizing the Doppler Effect, static surrounding materials have little impact on system performance.

Non-Contact Cardiac Motion Sensing

Rationale. The present disclosure utilizes cardiac motion as a new biometric to secure user authentication. Cardiac motion is a 3D automatic heart deformation caused by the self-excitement of the cardiac muscle. As shown in FIG. 2A, the human heart contains two upper chambers (atria) and two bottom chambers (ventricles). The successive contraction (systole) and relaxation (diastole) of both atria and ventricles circulate oxygen-rich blood throughout the whole human body. The contraction and relaxation comprise the cardiac motion cycle. In one cardiac cycle, ventricles relax and passively fill with blood in approximately 70% of their total volume from the atria through the open mitral valve.

Then, the heart muscles contract the atria to pump blood filling the remaining 20% of the ventricles. (Ventricles, at least, free up 10% of the volume for the contraction.) After that, the ventricles start to contract with all valves closed, and the blood volume remains unchanged. When the intraventricular pressures exceed the pressures within the aorta or pulmonary artery, blood is ejected from the ventricles and the heart volume reduces rapidly.

As shown in FIG. 2B, one cardiac motion cycle includes five distinct stages including: (1) ventricular filling (VF), (2) atrial systole (AS), (3) isovolumetric ventricular contraction (IC), (4) ventricular ejection (VE), and (5) isovolumetric ventricular relaxation (IR). These cycle stages are significantly different from each other in terms of the volumes, surface shape, movement dynamics (speed, acceleration, etc.), and 3D deformation of the heart. These stages also vary from person to person due to the change in size, position, anatomy of the heart, chest configuration and various other factors. No two persons have exactly the same heart, blood circulation system, and other related tissues. Therefore, cardiac motion is a unique identity marker for each individual. Moreover, since cardiac motion is intrinsically connected to multiple biological functions, it is extremely difficult to counterfeit or to be hidden for a living individual.

Feasibility. Non-contact monitoring of human body motion, such as respiration and heartbeat rates using a Doppler radar motion sensor, has gone through a few decades of scientific study. Efforts have been devoted to the development of radar front-end hardware, signal processing algorithms, and system on-chip/on-board integration. Compared with other techniques such as use of a non-contact laser vibrometer or an infrared imager that can only detect motion at body surface, it has been shown that a Doppler radar sensor can directly measure the motion of internal organs, such as the heart. However, research results in those works are incomprehensive for a real authentication system, e.g., the impact of random body movement is not considered. Although random body movement and clutter noise still require significant efforts to resolve, some progress has been achieved and preliminary clinical studies have been reported. However, existing cancellation approaches either compromise the quality of the baseband signals or require sweeping the carrier frequency and adjusting the target position, which is not applicable to capture high-fidelity cardiac motion in a real-world setup. Because of the sensitivity required for detection, along with difficulty in maintaining the original motion pattern during demodulation, most research using biomedical radar sensors have focused on detecting heart rate. Recently, some of our research results have proved that DC-coupled interferometry radar and Doppler radar with a digital-intermediate frequency (IF) architecture can avoid frequency-selective signal distortion and thus make it possible to recover accurate motion patterns using continuous-wave (CW) Doppler radar sensors.

Cardiac Scan Prototype

System Overview

By measuring the signal phase shift caused by physiological motion, biomedical radar can reveal heartbeat and respiration information. Compared with conventional biomedical radars that can only measure the rate of the heartbeat signal, an advantage of the radar sensor developed in the present disclosure is the use of a distortion-free front-end architecture and demodulation to measure cardiac motion pattern. A smart DC-coupled radar architecture was employed in the radar front-end to eliminate undesired DC offset and preserve the desired cardiac motion characteristic information.

Architecture with Dynamic DC Tuning

To monitor the cardiac motion pattern, a smart DC-coupled CW radar sensor was employed by taking advantage of real-time signal processing and mixed-signal design in modern devices. For cardiac motion sensing, the DC offset due to reflection from other parts of the body not related to cardiopulmonary activities may easily saturate the receiver and create frequency-dependent distortion, and is a factor for the processor (e.g., central intelligence unit) to handle.

Figure 3:
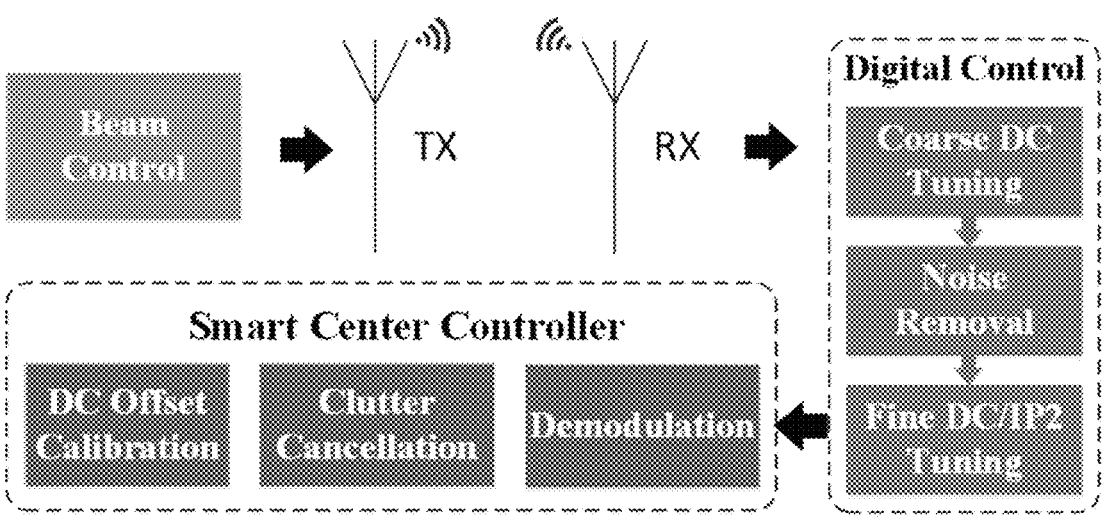
FIG. 3: Doppler radar sensor with adaptive DC tuning according to the present disclosure.

Smart DC tuning. As shown in FIG. 3, the DC-coupled adaptive tuning architecture may include RF coarse-tuning and base-band fine-tuning. For RF tuning, the electronically-controlled phase shifter and attenuator add a portion of the transmitted signal to the receiver signal to cancel most of the DC offset caused by clutter reflections. However, due to quadrature imbalance, the phase variation of the received signals, and the limited resolution of the phase shifter and the attenuator, the RF tuning cannot completely remove all the DC offsets. To further eliminate the remaining DC offsets, a baseband fine-tuning block was implemented to dynamically adjust the amplifier bias to the desired level that allows the maximum dynamic range. With the above DC tuning realized by a processor (e.g., the smart center controller depicted in FIG. 3) in real time, the radar will precisely measure cardiac motion pattern. The integration of the DC-tuning technique into portable devices can be addressed with the help of logic control circuits coordinated by, for example, the I2C bus and CMOS-integrated calibration DACs.

Optimal carrier frequency. Besides manipulating the penetration depth, radar carrier frequency also determines the modulation sensitivity. Experiments were first carried out to compare the performance of carrier frequencies ranging from 2.4 GHz to 40 GHz. It should be noted that increasing the carrier frequency beyond 40 GHz may not help because as the wavelength approaches physiological motion amplitude, strong nonlinear phase modulation will generate harmonic interference.

Electronic beam control. In embodiments of the present disclosure, cardiac sensing may be realized from different angles to obtain sufficient information for biometrics applications. Also, multiple radars around a subject may "probe" cardiac signals simultaneously. To achieve this, it is advantageous for a radar capable of configuring the radiation beam to point at the location of interest. As shown in FIG. 3, digital beam control may be implemented on the radar front-end. Conventional beamforming systems directly adjust the phase and amplitude of the signal of each element antenna. We demonstrated that it is much more convenient to simultaneously adjust the phase and amplitude in the complex domain than to adjust them separately. For a complex signal x=exp(−j2πft) sent into each element antenna (where f is the signal frequency), a vector multiplier was used to realize phase and amplitude modulation by first splitting the signal into in- and out-of-phase components and then by multiplying each one using a variable gain amplifier. Finally, by adding the amplified in- and out-of-phase components together, complex modulation to the original signal can be achieved, thereby effectively realizing radar beam control. To align the radar beam with the user, a laser pointer can be used to indicate the beam direction.

Radio Signal Processing Schemes

Scheme Overview

Figure 4:
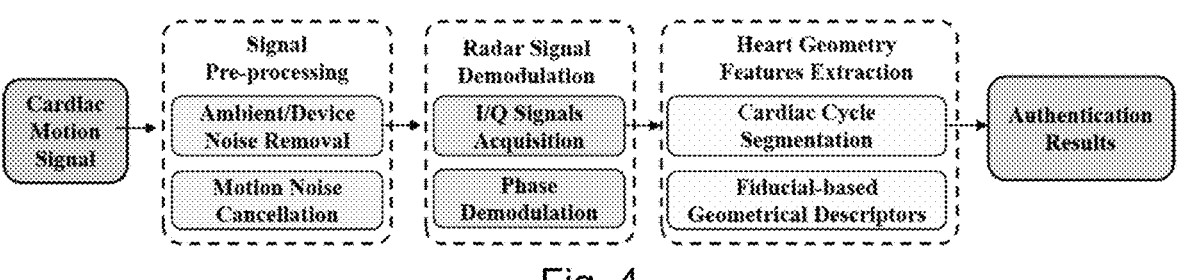
FIG. 4: A flowchart of Cardiac Scan, a heart-biometric-based continuous user authentication system according to an embodiment of the present disclosure.

In this section, exemplary radio signal processing schemes are presented and exemplary user authentication methods for achieving secure and usable authentication results are described. As depicted in FIG. 4, an exemplary embodiment of the present approach is mainly comprised of three modules. First, the original sequential signal was preprocessed for noise reduction. Second, de-noising aware radar signal demodulation was performed. Third, fiducial-based descriptors were extracted using heart geometry features. Lastly, authentication results were obtained. Note that existing heart-based biometrics, such as ECG, record the electrical activity of the heart, whose descriptors are extracted on the basis of the QRS complex. As a new biometric modality, the presently-disclosed non-contact cardiac motion technique is substantially different from the typical ECG signal in that it is a direct heart motion activity measured by an RF sensor.

Pre-Processing

Pre-processing may be performed to reduce the noise level in the cardiac signal and simultaneously prevent the waveform from distortion. Such noise may include low-band components (e.g., baseline wander), high-band components (e.g., power-line interference), and unpredictable-band components (e.g., arbitrary motion in the scene). Considering diverse and known frequency bands of the noise spectrum, the present disclosure addresses noise level reduction in two areas: (1) one-pass noise reduction techniques (e.g., a Butterworth bandpass filter); and (2) adaptive noise canceling techniques (e.g., a normalized least mean square adaptive filter). These techniques have also been successfully applied in bio-artifact reduction.

De-Noising-Aware Radar Demodulation

Traditional Doppler radar, which is optimized for speed detection, faces challenges when the movement pattern has a very low frequency or stationary components. As such, a new signal demodulation technique was developed and found to be advantageous for distortion-free cardiac motion sensing.

Challenges in signal demodulation. The Doppler radar sensor transmits the continuous-wave signal T(t)

$$T(t)=A_T\cos(\omega t+\phi(t)). \tag{1}$$

Then, the received signal is represented as R(t):

$$R(t) = A_R\cos\left[\omega t - \frac{4\pi d_0}{\lambda} - \frac{4\pi x(t)}{\lambda} + \phi\left(t - \frac{2d_0}{c}\right)\right], \tag{2}$$

where A is the amplitude, $\lambda$ is the wavelength, c is the speed of light, $\omega$ represents the angular velocity, $\phi(t)$ is the time-varying phase, $d_0$ is the distance between the Doppler radar and the subject, and x(t) denotes the time-varying displacement caused by cardiac motion. Then, two baseband signals, the in-phase signal I(t) and quadrature signal Q(t) can be derived from R(t):

$$I(t) = A_I \cos\left[\frac{4\pi x(t)}{\lambda} + \frac{4\pi d_0}{\lambda} - \phi\left(t - \frac{2d_0}{c}\right)\right] + DC_I, \quad (3)$$

Q(t) is the quadrature signal:

$$Q(t) = A_Q \sin\left[\frac{4\pi x(t)}{\lambda} + \frac{4\pi d_0}{\lambda} - \phi\left(t - \frac{2d_0}{c}\right) + \phi_0\right] + DC_Q \quad (4)$$

where $A_I$ and $A_Q$ are the amplitude of the in-phase signal and the quadrature signal, respectively, $DC_I$ and $DC_Q$ are the DC offsets in I/Q channels, respectively, and $\phi_0$ is the phase offset between I(t) and Q(t). In a test embodiment, the baseband radar signals, I(t) and Q(t), were sampled using an NI USB-6008 at 100 Hz.

For simplicity, the constant phase offset $4\pi d_0/\lambda + \phi(t-2d_0/c)$ in Eq. (3) and Eq. (4) may be neglected. The gain imbalance may be assumed to be 1 (i.e., the ratio $A_I$ and $Q_Q$ is 1), and the phase imbalance ($\phi_0$) may be assumed to be 0. Thus, Eq. (3) and Eq. (4) can be simplified as:

$$\begin{cases} I(t) = A_0 \cos\left(\frac{4\pi x(t)}{\lambda}\right) + DC_I \\ Q(t) = A_0 \sin\left(\frac{4\pi x(t)}{\lambda}\right) + DC_Q \end{cases} \quad (5)$$

According to trigonometric identities, Eq. (5) into Eq. (6) can be transformed:

$$\left(\frac{I(t) - DC_I}{A_0}\right)^2 + \left(\frac{Q(t) - DC_Q}{A_0}\right)^2 = 1, \quad (6)$$

which can be interpreted that the samples of I/Q channels stay on a circle whose center is $(DC_I, DC_Q)$ with a radius of $A_0$. Then, a least squares optimization is employed to obtain the circle and obtain the three unknown parameters: $DC_I$ and $DC_Q$, and $A_0$.

After identifying the DC component offsets, the displacement signal x(t) can be derived using the arctangent demodulation method:

$$x(t) = \arctan\left(\frac{Q(t) - DC_Q}{I(t) - DC_I} \times \frac{4\pi}{\lambda}\right). \quad (7)$$

Traditionally, to detect the weak physiological signal x(t), the small-angle approach was used, which suffers from two inherent problems. First, when the distance between the target and the radar sensor changes, the detection sensitivity will also change, resulting in alternating optimum and null points. Second, nonlinear harmonics and intermodulation products would appear when movement amplitudes are comparable to the carrier wavelength. To solve these problems, an arctangent demodulation approach was considered by calculating arctan $$\left[\frac{Q(t)}{I(t)}\right],$$

assuming $DC_I$ and $DC_Q$ can be properly calibrated. Unfortunately, a direct arctangent function has a co-domain range of $$\left(-\frac{\pi}{2}, \frac{\pi}{2}\right),$$

Once the demodulation exceeds this range, phase unwrapping is required, which is challenging in practical detection when noise is strong and the movement amplitude is large. This is especially a problem when random body motion exists, which introduces a significant phase change that could easily go beyond multiples of $2\pi$.

Phase demodulation solution. To overcome the limit of arctangent demodulation, an extended "differentiate and cross-multiply" (DACM) technique may be used to avoid the phase unwrapping problem. The technique computes a derivative to the arctangent-demodulated phase information first:

$$\omega(t) = \frac{d}{d_t}\left[\arctan\frac{Q(t)}{I(t)}\right] = \frac{I(t)\dot{Q}(t) - \dot{I}(t)Q(t)}{I(t)^2 + Q(t)^2}, \quad (8)$$

where $\omega(t)$ is related to the velocity function of the cardiac motion, and $\dot{Q}(t)$ and $\dot{I}(t)$ denote the time derivative of Q(t) and I(t), respectively. To reconstruct the desired phase information, which represents cardiac motion, integration can be applied to the above result. Therefore, the signal phase can be recovered in the digital domain as:

$$\Phi_\theta[n] = \sum_{k=2}^{n} \frac{I[k]\Delta Q[k] - \Delta I[k]Q[k]}{I^2[k] + Q^2[k]}, \quad (9)$$

where I[k] and Q[k] are the discrete samples of the I/Q channel outputs. $\Delta I[k]=I[k]-I[k-1]$ and $\Delta Q[k]=Q[k]-Q[k-1]$. The operation block diagram is also shown in the "smart center controller" of FIG. 3. By introducing an accumulation procedure, noise can be effectively suppressed. Once $\Phi_\theta[n]$ is obtained, the cardiac motion x[n] can be linearly obtained based on a single scale calibration.

Continuous Authentication

Heart Geometric Features

Segmentation. To extract the invariant descriptors from the cardiac motion signal of the subject, the periodical signal sequence was segmented into discrete frames. For fiducial descriptors, there exist literature where multiple cardiac cycles were used. We have investigated the performance with various numbers of cardiac motion cycles. Though each segment (see FIG. 5) includes all five heartbeat motion stages, the variations across individuals within one cardiac cycle may not be sufficient for differentiation. This segmentation with disparate cardiac motion cycles benefits the signal alignment because it associates the segment with the physiological cardiac motion in one or multiple cycles.

Fiducial descriptors. The fiducial-based method extracts intrinsic geometrical descriptors (e.g., temporal, amplitude, area, angle) from fiducial points in the cardiac motion signal. Specifically, fiducial points are the biomarkers with physical meaning in the clinic during the cardiac motion cycle. Fiducial points contain the biological information that is unique and non-volatile for individuals, and are also independent of the sensor location or state of the individual such as anxiety, nervousness, or excitement. On the other hand, non-fiducial-based methods focus on the non-physical attribute features, which fail to reflect the intrinsic geometric features of the heart. Also, such non-fiducial methods are computationally demanding and apt to be interfered with by parameters setting, making non-fiducial-based methods less effective for continuous real-time authentication. In the fiducial-based method, the cardiac displacement signal is well matched to the cardiac activity rationale described above (under the heading "Design Considerations"). The first stage, Ventricular Filling (VF), is when the semilunar valves (SV) close and the atrioventricular valves (AV) open. The whole heart is relaxed and the blood charges into atria as well as ventricles, resulting in the outward expansion of the heart. The second stage, Atrial Systole (AS), is when atria contract to pump their contained blood into ventricles. The heart will contract inward first due to the emptying of atria. It will expand outward again because the extra blood in atria is squeezed into ventricles (SV will close to prevent blood from flowing into arteries). The third stage, Isovolumetric Ventricular Contraction (IC), is when ventricles begin to contract and SV/AV close. Since there is no change in volume, no significant displacement occurs. Lastly, Ventricular Ejection (VE), is when SV opens and ventricles are contracting and forcing blood into arteries. As a result, the heart will contract inward. During the fifth stage, Isovolumetric Ventricular Relaxation (IR), ventricles finish the blood ejection, stop contracting, and begin to relax. This cycle ends and begins anew.

Figure 5:
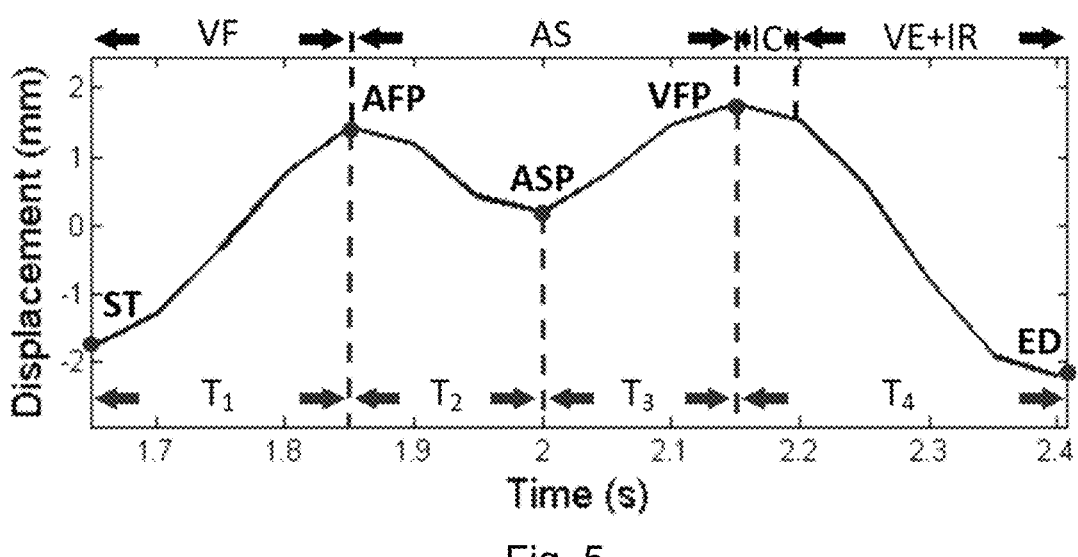
FIG. 5: Segmentation and fiducial points illustration.

FIG. 5 shows a complete segment and the changes of the cardiac displacement. Based on the cycle description above, the signal is typically further split into four sub-frames, each of which is labeled with the corresponding stage. We will refer to ST and ED as the starting point and ending point of the segment. An exemplary set of fiducial points suitable for use in the present technique comprises AFP, ASP, and VFP, described as:

AFP: the first maximum point in the segment, which indicates the end of the VF stage and the onset of the AS period where the atrial muscles contract to squeeze the blood into the ventricles.

VFP: the second maximum point in the segment, which locates at the end of the AS stage. The blood flows into the ventricles and reaches the largest volume.

ASP: the local minimum point between AFP and VFP. It represents the end of atria contraction and the start of ventricles expansion.

Table 1 lists the descriptors based on the above fiducial points. Note that all the time descriptors $T_i$ are normalized by the duration of one cardiac cycle, such that these descriptors are independent of heart rate.

TABLE 1

| List | Fiducial-based descriptors. Descriptor Definition |
|---|---|
| $T_1$ | Normalized Time interval between ST and AFP. |
| $T_2$ | Normalized Time interval between AFP and ASP. |
| $T_3$ | Normalized Time interval between ASP and VFP. |
| $T_4$ | Normalized Time interval between VFP and ED. |
| $H_1$ | Displacement difference between ST and AFP. |
| $H_2$ | Displacement difference between AFP and ASP. |
| $H_3$ | Displacement difference between ASP and VFP. |
| $H_4$ | Displacement difference between VFP and ED. |

Figure 6:
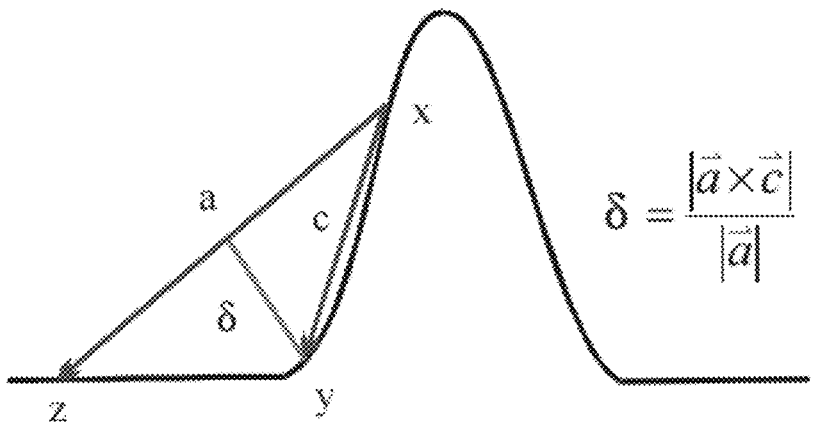
FIG. 6: The radius of curvature is calculated as the vector-cross product between the two directed line segments.

Fiducial point extraction is of great importance to accurately locate the feature point. Due to the potential clutter noise, the radius of curvature is more robust than the more straight-forward local extreme point or signal derivatives. Specifically, three points were selected, X, Y, and Z, with a fixed time interval along the time sequence. The minimum (maximum) radius of curvature in the corresponding region is found by maximizing (minimizing) the value of $\delta$ using the vector cross product between the two directed line segments, as shown in FIG. 6.

Continuous Authentication Protocol

One time validation of a user's identity, referred to as static authentication, has shown its vulnerability to attacks. Specifically, malicious adversaries may access the system that has been logged in by an authentic user when the authentic user is not nearby. Unlike static authentication, continuous authentication represents a new security mechanism which continuously monitors the user's trait and use it as a basis to re-authenticate periodically throughout the login session. Therefore, continuous authentication significantly enhances the security level of systems. Cardiac Scan enables unobtrusive and non-contact continuous authentication with the radio frequency (RF) interrogation, during which RF signals transmit and measure the human target continuously. By demodulating the received echo signal, the cardiac motion pattern of the user can be extracted. In what follows, we will discuss continuous authentication parameters and three typical scenarios.

Continuous Authentication Parameters. Two parameters, refreshing interval $T_r$ and negative tolerance threshold $Th_{nt}$, may be important in continuous authentication, which are unique compared to static authentication.

Refreshing interval $T_r$: The refreshing interval, $T_r$, is the interval between two consecutive authentications. The appropriate choice of $T_r$ has an impact on the performance and usability of continuous authentication. If $T_r$ is too large, malicious adversaries may not be detected in time, thus leading to severe security issues. On the other hand, if $T_r$ is too small, some random activities (e.g., making phone calls, drinking water, turning around) or rhythmic body movements (e.g., listening to music) may compromise the system's recognition accuracy due to false alarms. Considering these random activities usually take about several seconds, in an exemplary embodiment, the refreshing interval was selected as 5 seconds. Refreshing intervals that are higher or lower are acceptable and within the scope of the present disclosure. Note that the refreshing interval should be differentiated from the authentication time $T_a$. The latter is defined as the time duration for a single authentication process and is further discussed below.

False negative tolerance threshold $T_{nt}$: Usability may be a consideration in continuous authentication to make sure the authentic user will not frequently be interrupted by mistakenly logging out of the system. In other words, it may be preferable to avoid the false negative event, which is the incorrect classification of an authentic user as an adversary due to motion artifacts. It was noted that false negative events are rare and appear sparsely in the Cardiac Scan test embodiment, which means there is a low probability that more than one "classified as adversary" event occurs consecutively when the authentic user is present. On the other hand, when an adversary is present, the "classified as adversary" event will occur consecutively. After observing such phenomena, we defined a false negative tolerance threshold as the number of permitted consecutive "classified as adversary" events. Empirically, the value for this threshold may be selected as 1 or 2. The larger value setting is more tolerant to false negative and the smaller value setting is more sensitive to risk. In the following exemplary scenarios, a threshold setting of 1 was adopted because the usability of continuous authentication would not be compromised given the low false negative rate of Cardiac Scan. Also, this setting maintains a high sensitivity to unauthorized access. However, it should be recognized that other values (higher or lower) may be used.

Continuous Authentication Scenarios. Three exemplary scenarios were devised for the Cardiac Scan test embodiment-enabled continuous authentication, including Authentic user is present, Authentic user leaves, and Adversary is present.

Figure 7:
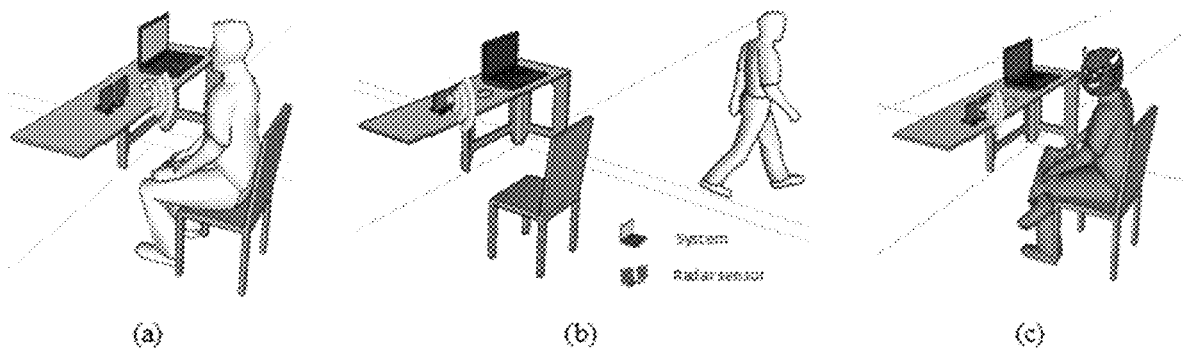
FIG. 7: Three scenarios: (a) Authentic user is present, the system remains unlocked. (b) Authentic user leaves, the system locks up. (c) Adversary is present, the system locks up. Light screen: system is unlocked. Dark screen: system is locked.

Authentic user is present: When an authentic user was logged into the system and was present within the range of the radar sensor, Cardiac Scan was able to detect whether cardiac motions were from the same person who was initially authorized. Thus, permission to use the system could be continuously granted without any interruption, unless the user logged off intentionally or leaves, as shown in FIG. 7(a). By designing the false negative tolerance, Cardiac Scan allowed one single "classified as adversary" event given that the classification results just before and after this event were both positive as "classified as authentic user." In the case where two or more than two consecutive "classified as adversary" events occur, though this has a low probability, Cardiac Scan will log out the initial user. Under such a circumstance, the user may then be re-authenticated by confirming his identity again using other complementary existing approaches, such as a PIN or fingerprint. Note that for scenarios which have a specific requirement, the system tolerance level can be adjusted by changing the value of $Th_{nt}$.

Authentic user leaves: When the authentic user was away from the system and the radar sensor detected the user's absence, as shown in FIG. 7(b), Cardiac Scan will first check whether the user has logged off and the system has been locked up. If so, Cardiac Scan will classify the user's absence as a legitimate action and no further action needs to be taken. Otherwise, the system is at risk of unauthorized access, hence necessary actions such as locking the session, logging out the original user, or notifying the administrator, which depend on the system policy, may be considered to address the security risks.

Adversary is present: In this scenario, an unauthorized adversary (the dark user depicted in FIG. 7(c)) was present and close to the system, and the system had been logged in initially by an authentic user. This can happen when the authentic user is under the coercion attack and being forced to be present or the adversary takes over the system before the system automatically locks up when the authentic user leaves. Therefore, immediate action is demanded to keep the adversary outside the system and prevent the leakage of sensitive information. In this case, Cardiac Scan will immediately log out the initial user and lock the system once $Th_{nt}$ is exceeded.

EXPERIMENTS AND VALIDATION

Experimental Setting

Figure 8:
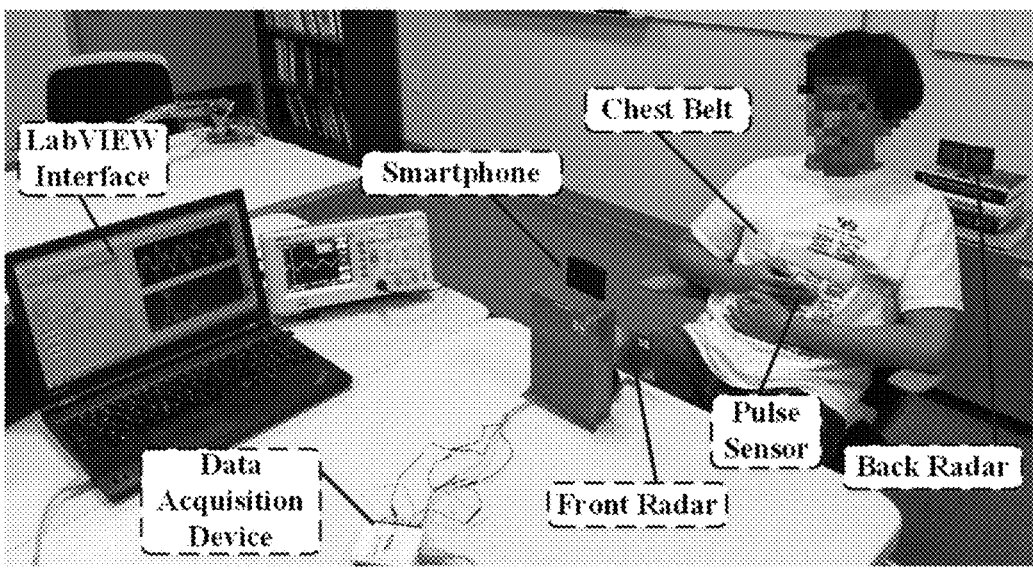
FIG. 8: Experimental setup for cardiac motion sensing according to an embodiment of the present disclosure. A subject is sitting one meter away from both radar sensors, a chest belt and a pulsed sensor is attached to the subject.

A pilot study was conducted to prove identifiability in cardiac motion. A test embodiment of the disclosed Cardiac Scan system was developed for the study. The test system operated at the frequency of 2.4 GHz with the bandwidth of 5 kHz. The sampling frequency was 40 Hz. Though Wi-Fi and Bluetooth also work at 2.4 GHz, the cardiac motion signal would not be interfered with because the motion information to be detected is only a few Hertz, which means both received signals and transmitted signals are only separated by a few Hertz, while other signals from potential interferences (e.g., WiFi and Bluetooth) have a much higher frequency separation and are conveniently rejected by the base-band signals. In other words, both transmitted signals and received signals are "coherent," whereas other signals are not coherent with transmitted signals. The Doppler radar had two antennas with the beam width of 45 degrees, i.e., one for the transmitter and one for the receiver. The power consumption of the test radar was only 650 mW with 5 V voltage and 130 mA current. Note that the transmission power level is within the human safety range because it is almost a thousand times less than the peak power of an ordinary global system for mobile communications (GSM) cellphone. The experimental setup is shown in FIG. 8, a subject sat in a chair in a relaxed condition. The customized Doppler radar sensor was placed in front of the subject at a distance of 1 m. A smartphone was placed close to the radar to record the subject identity and label the ground truth. The radar signal demodulation was done using a laptop equipped with Intel i7-3770 CPU @ 3.4 GHz. Motion compensation was carried out for the baseband complex signal obtained from subjects who breathed normally but randomly moved their body. A pulse sensor (UFI 1010 pulse transducer) was attached to the subject's finger to provide a heartbeat reference. A chest belt (UFI 1132 piezo-electric respiration transducer) was used to provide a respiration reference.

Data Collection

As described above, the project evaluation used a strategically developed experiment that involved a cohort of participants. Seventy-eight healthy subjects (46 males and 32 females) with ages in the range of 16-54 participated in the study. Their weights were between 42-83 kg. None of them had any heart disease. Each subject had 20 trials, and each trial lasted eight seconds including 8 to 10 cardiac cycles. In each trial, all subjects were required to sit in front of the radar, unless specified in the evaluation, to get the cardiac motion signals collected. Therefore, in total there were 20 sets of data containing 14,886 cardiac cycle samples in the evaluation.

User Classification

To prove the identifiability in cardiac motion, dynamic time warping (DTW) was used as the similarity matching metric. Support vector machine (SVM) with a radial basis function (RBF) kernel classifier and 10-fold cross validation were employed for the 20 sets of data in the evaluation, among which 18 were for the training and 2 for the testing. The choice of the classifier will be further discussed below. In authentication, initially, the owner's cardiac motion template was stored in the system. Then, unknown users attempted to access the system by keeping still in front of the radar. Since there were total 78 participants, and each participant acted as an owner once while remaining participants acted as attackers.

Body Movement Interference Suppression

Compared with cardiac motion, body movement may result in a large perturbation to the output DC offset, and thus confuse the radar demodulation algorithm or even saturate the baseband circuit. In the experiment, the time-domain signal had fluctuations due to the random body motion. As a result, strong near-DC spectral components were observed and the heartbeat was invisible in the spectrum. Simply reducing the front-end gain, as adopted in some communication systems, does not work because the radar will lose the sensitivity to the weak cardiac motion signal.

Because biomedical radar can detect cardiac motion from four sides of a human body, multiple radars can be installed at different locations around the human body to cancel out random body motion based on the different patterns of body motion and cardiac motion. In the view of the two radars, the heartbeat-and-respiration-caused body movements are in phase, while the random body movements are out of phase. In the test setting, two radars were detecting from the front and the back of the body. When the body was drifting toward one radar, it is moving away from the other; whereas heartbeat presents similar expansion/contraction patterns to the two radars. Therefore, random body motion creates an opposite Doppler frequency shift to the signals of the radars, while cardiac motion leads to the same polarity. By properly combining the low-speed baseband signals from the radars, one type of motion can be canceled and the other type will be enhanced. Note that although the random body movement can exist in the direction perpendicular to the radar direction, the body movement cancellation method used in the test system still works effectively because only the movement in the radar direction is relevant for the cardiac motion detection.

Signal Validation

We verified the validity of the collected data from the test system. When the radar sensor detected cardiac motion, the fingertip sensor simultaneously collected a signal as the ground truth signal. Both the radar sensor and fingertip pulse sensor were sampled at 40 Hz. We observed that the cardiac motion cycles were well aligned, each of which closely matched the peaks in the fingertip signal. So we verified that our system could accurately detect the cardiac motion signal in a non-contact way.

Evaluation Results

As a potential breakthrough technology, it is necessary to evaluate the performance, flexibility, and vulnerabilities in practice of Cardiac Scan. Note that all the performance results were obtained after random body movement suppression except the one specified as "before random body movement suppression" in the evaluation of subjects in motion. We employed several statistics to describe the performance of Cardiac Scan.

Accuracy

Balanced Accuracy and F-measure. We provided the F-measure accuracy (F1 score) and balanced accuracy (BAC) for the accuracy measurement, both of which are non-sensitive to class distribution and can avoid misleading accuracy measurement when the true class distribution is unbalanced. F1 score is known as the harmonic mean of precision and recall, precision p is the number of true positive (TP) divided by the number of positive calls (TP+FP) while recall r (a.k.a. true positive rate) is the number of true positive (TP) divided by the number of condition positives (TP+FN) where FP is false positive and FN is false negative. F1 score reaches its best value at 1 and worst at 0. Simply, F1 score is defined as follows:

$$F_1(\%) = 2 \cdot \frac{\text{precision} \cdot \text{recall}}{\text{precison} + \text{recall}} = \frac{2TP}{2TP + FP + FN}. \qquad (10)$$

And BAC is the equal combination of true positive rate (TPR) and true negative rate (TNR), which is defined as:

$$BAC\ (\%) = 0.5 * TPR + 0.5 * TNR = \frac{0.5 * TP}{TP + FN} + \frac{0.5 * TN}{TN + FP}, \qquad (11)$$

where TN is true negative.

Table 2 shows the average F1 and BAC accuracies of the authentication with different configurations. BAC achieve 95.56%, 97.27%, and 98.61% with the standard deviation (STD) of 0.92%, 0.65% and 0.38% for 1 cycle, 2 cycles, and 4 cycles, respectively. F1 values are exactly mean values of BAC, which are 95.56%, 97.27%, and 98.61% for 1 cycle, 2 cycles, and 4 cycles. The results indicate that the increase of segment length improves accuracies. Furthermore, the performance benefits from the longer segment length and achieves the best accuracy of 98.61%. Note that the false positive events are not produced by the same pairs.

TABLE 2

| Accuracy comparison for different cardiac cycles. | | | |
|---|---|---|---|
| List | 1 cycle | 2 cycles | 4 cycles |
| F1 (%) | 95.56 | 97.27 | 98.61 |
| BAC (%) | 95.56 ± 0.92 | 97.27 ± 0.65 | 98.61 ± 0.38 |

Figure 9:
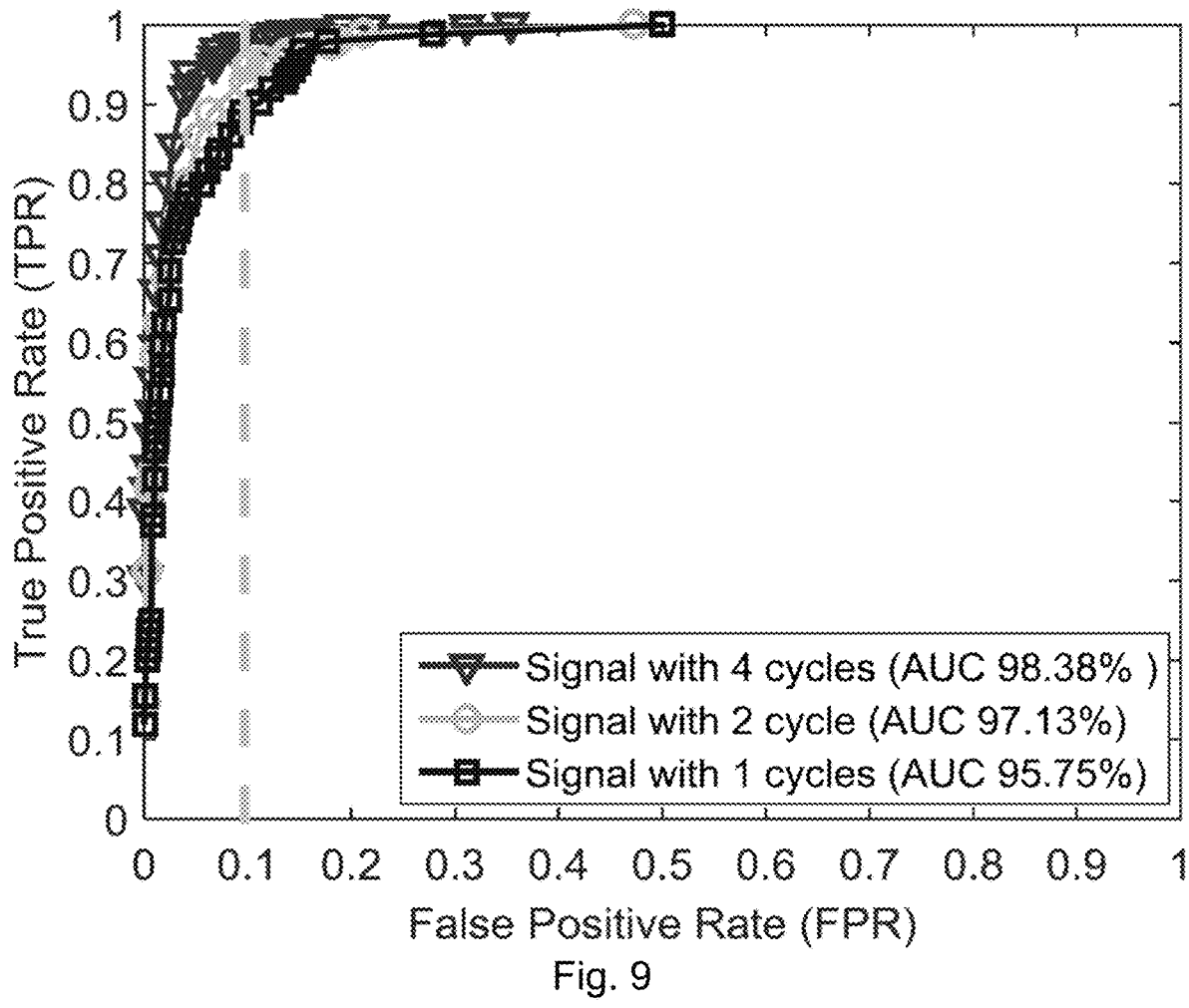
FIG. 9: The average ROC curves with AUC of 78 subjects with different number of cardiac cycles.

Receiver Operating Characteristic. Receiver operating characteristic curve is created by plotting the true positive rate (TPR) against the false positive rate (FPR) at various threshold settings, which illustrates the performance of a binary classifier system as its discrimination threshold is varied. FIG. 9 depicts the average ROC curves of 78 subjects with different segment lengths. The signal with 4 cycles exhibits the best performance among three different segmentation configurations, which is consistent with the results of BAC and F1. Specifically, the corresponding area-under-curve (AUC) for each curve is also calculated as 98.38%, 97.13%, and 95.75% for signals with 4 cycles, 2 cycles, and 1 cycle, respectively.

Figure 10:
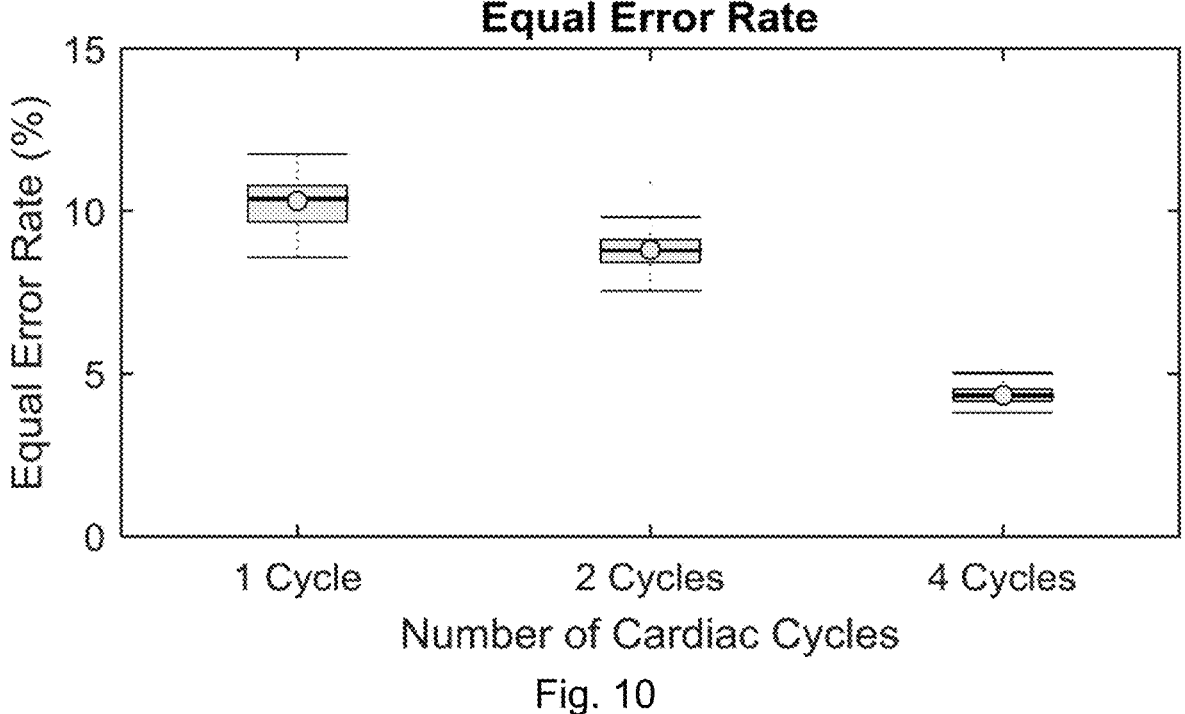
FIG. 10: The EER with a different number of cardiac cycles. Four cardiac cycles configuration has the lowest EER.

Equal Error Rate. The equal error rate (EER) is a performance metric for authentication systems. It is a rate when the operating threshold for the accept and reject decision is adjusted such that the acceptance error (false positive rate, FPR) and rejection error (false negative rate, FNR) becomes equal. The lower the equal error rate value, the higher the accuracy. FIG. 10 depicts the EER of 78 subjects with different segment lengths. The mean of EER is 10.37%, 8.79%, and 4.42% for 1, 2, and 4 cycles, respectively.

TABLE 3

| Comparison of classifiers. | | | | |
| --- | --- | --- | --- | --- |
| | kNN | SVM (linear) | SVM (polynomial) | SVM (RBF) |
| BAC (%) | 90.85 | 95.17 | 96.65 | 98.61 |
| EER (%) | 12.27 | 9.13 | 6.39 | 4.42 |

Classifier Impact. We compared two different classification techniques to select the best classifier for the test application, including support vector machine (SVM) and k nearest neighbors (kNN). A linear, a polynomial, and a radial basis function (RBF) kernel were adopted for SVM. Parameters of each classifier were tuned to achieve the best performance. The number of nearest neighbors k=4, and $\gamma$ and C of RBF function were 0.001 and 10000, respectively. Four cycles of cardiac motion were employed in this evaluation. The BAC and EER results are shown in Table 3. KNN had the lowest BAC of 90.85% and highest EER of 12.27%. SVM with RBF kernel had the highest BAC of 98.61% and lowest EER of 4.42%. SVM with linear and polynomial kernel had BAC of 95.17% and 96.65%, EER of 9.13% and 6.39%. The SVM with RBF kernel showed the best performance, which was adopted for the analysis below.

Authentication Time

Another performance metric for a user authentication system is the authentication time. Generally, a practical user authentication mechanism should not only be accurate in identifying the legitimate owners and the invalid attackers, but also time-efficient in processing authentication. We specifically defined the authentication time in terms of the total time elapsed, $T_a$, to make a final prediction for each user access attempt:

$$T_a = T_{cardiac\_motion\_sensing} + T_{processing}, \qquad (12)$$

where $T_{cardiac\_motion\_sensing}$ is the minimum time that Cardiac Scan needs to collect the cardiac motion signals with the radar device. This depends on the number of cardiac cycles required to identify users. $T_{processing}$ is the time needed to process cardiac motion signals, including demodulation, denoise, feature extraction, and user authentication.

Figure 11:
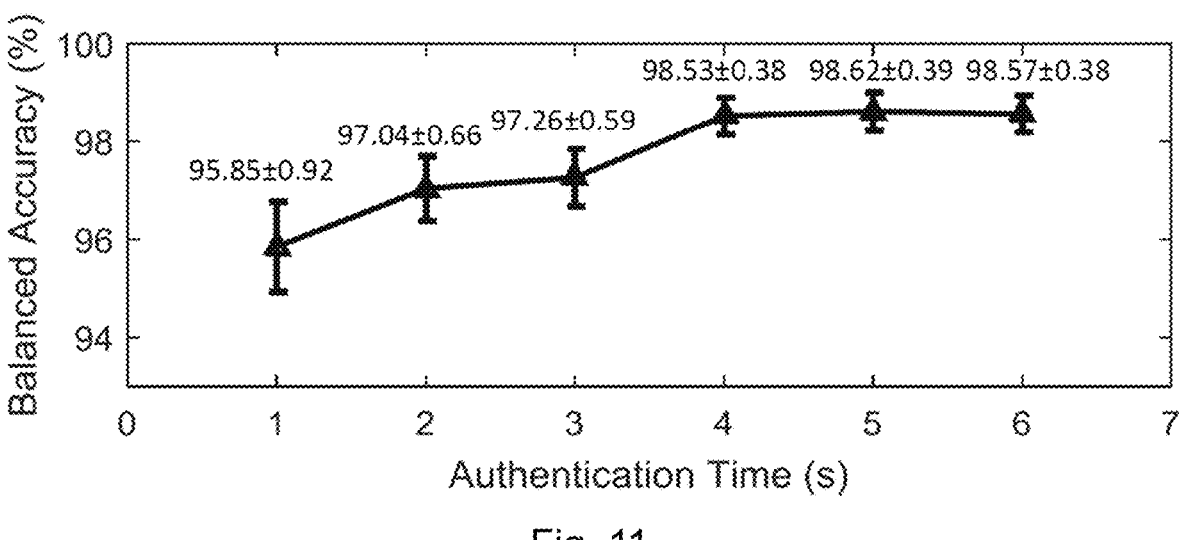
FIG. 11: The balanced accuracy of 78 subjects with different authentication time showing authentication with 4 second duration was the optimal choice for the test system.

To evaluate the authentication time efficiency, we applied different time restrictions on authentication time. Twenty subjects repeated the experiment with six different duration setups from 1 second to 6 seconds with increments of 1 second. The balanced accuracy with different authentication time is illustrated in FIG. 11. The error bars are the STD of BAC among 78 subjects. We observed that an authentication duration less than 3 seconds was not long enough for reliable authentication, with low BAC (95.85% for 1 second, 97.04% for 2 seconds, 97.26% for 3 seconds) and high STD (0.92% for 1 second, 0.66% for 2 seconds, 0.59% for 3 seconds). The performance was improved when the duration was increased to 4 seconds with BAC of 98.53% and STD of 0.38%. Generally speaking, the accuracy increases with the longer authentication time. However, when the duration is greater than 4 seconds, the performance improvement was not significant. To be specific, BAC of 98.62% and 98.57%, and STD of 0.39% and 0.38% were for 5 seconds and 6 seconds, respectively. Here again, these values are exemplary and are applicable to the test embodiment.

We also provided the growth rate for different authentication duration to find the optimal duration in Table 4. The growth rate is calculated by the accuracy in the current duration and the previous duration. The growth rates for each second are 1.23%, 0.23%, 1.29%, 0.09% and −0.05%. Note that the duration of 4 seconds has the largest growth rate, and seems to be a significant turning point.

TABLE 4

| The BAC and growth rate. | | | | | | |
| --- | --- | --- | --- | --- | --- | --- |
| Duration | 1 sec | 2 sec | 3 sec | 4 sec | 5 sec | 6 sec |
| BAC (%) | 95.85 | 97.04 | 97.26 | 98.53 | 98.62 | 98.57 |
| Growth (%) | — | 1.23 | .23 | 1.29 | 0.09 | −0.05 |

Evaluation in Complex Conditions

Another evaluation aspect is user experience. Typically, user experience can be defined as: a person's perceptions and responses that result from the use and/or anticipated use of a product, system, or service. Therefore, the evaluation of user experience mainly focuses on the attitude/feeling of a person towards a product/system during its intended practical use. Traditionally, several methods have been widely adopted to maximally collect the feedback of a person on the product/system, such as interview, observation, or survey. One unique aspect of the Cardiac Scan from many conventional authentication methods is that it is completely non-contact and passive to the user. Under normal conditions, the cardiac motion is not controllable or visible (even though it may be felt) to the user, which means that in most cases, the user will not be conscious of the interaction with the system in daily use. We also evaluated usability with four variations: sensor distance, sensor alignment, emotional state, and subject in motion.

Figure 12:
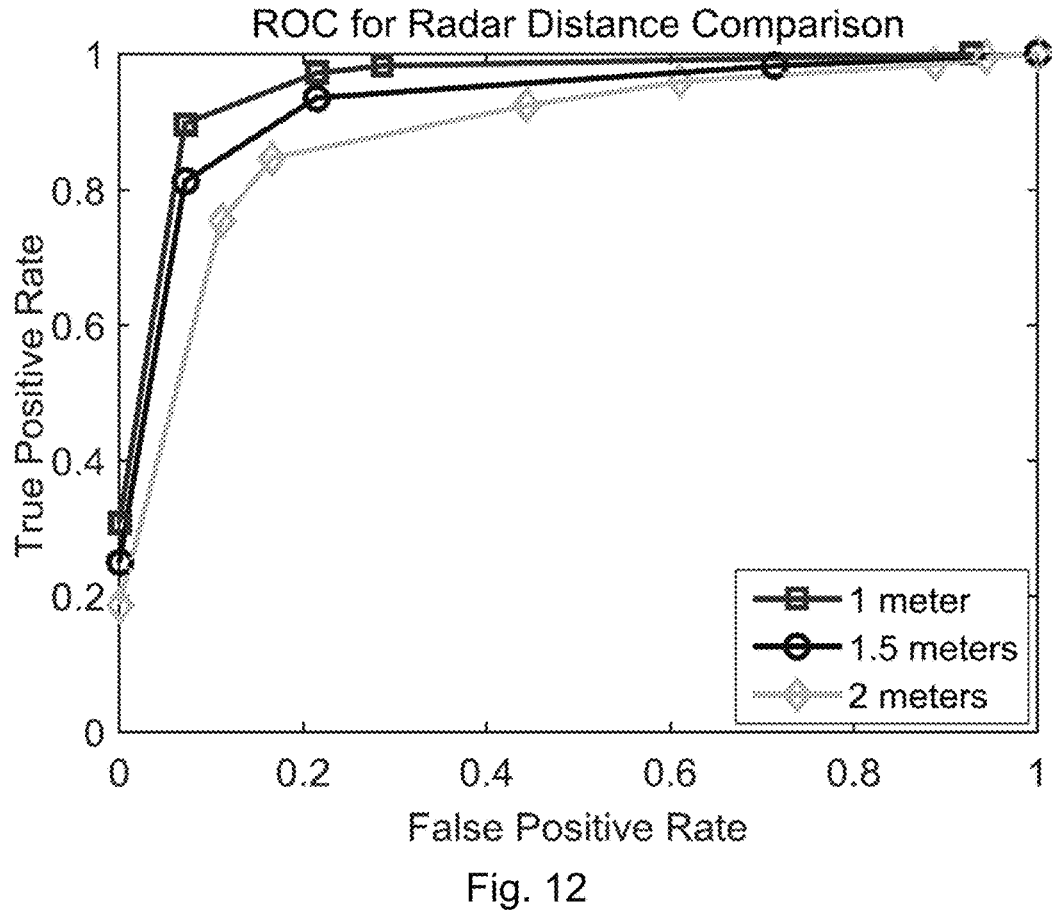
FIG. 12: The ROC of different radar distances.

Distance Impact: We evaluated the impact of distance on the accuracy of cardiac motion authentication. The distance is defined as the length between the subject and the antenna of Doppler radar sensor. To make the Doppler radar sensor safe for human applications, we have restricted the transmission power, so that the effective distance for the Doppler radar is 2 meters. Based on our observation, the amplitude of the baseband radar I/Q signal is inversely proportional to the distance between the subject and Doppler radar sensor. When the subject is far away from the Doppler radar sensor, the amplitude diminishes because it is difficult for the sensor to capture the slight cardiac motion. FIG. 12 illustrates the ROC of different radar distance comparison. Not surprisingly, the closest distance of 1 m has the best recognition performance. The accuracy decreases with the increasing distance between radar and subject.

Figure 13:
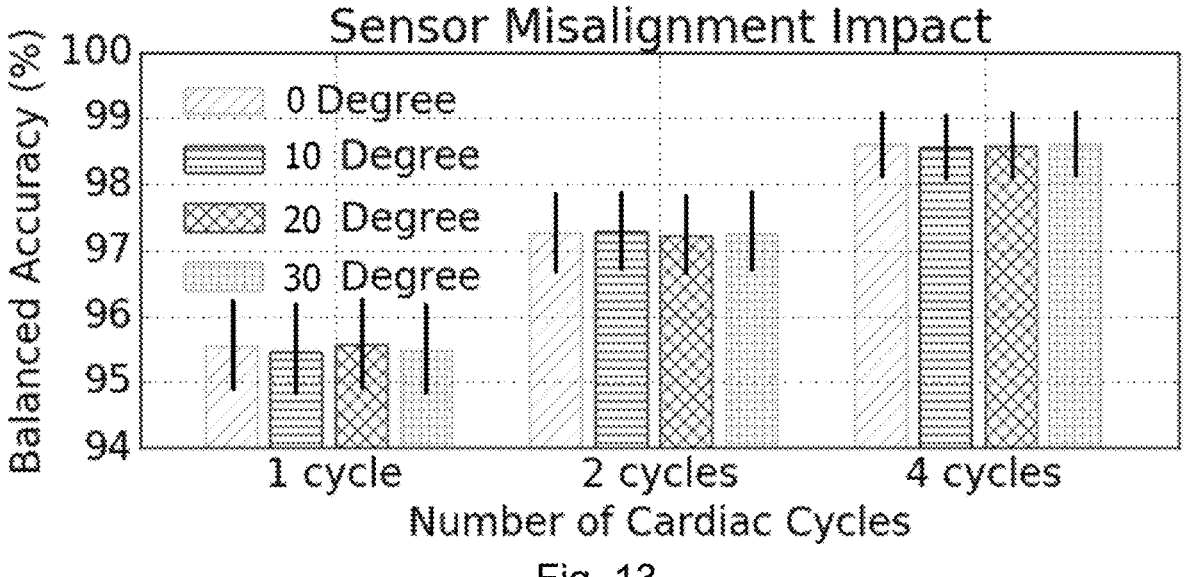
FIG. 13: The BAC comparison for misalignment.

Location Sensitivity: As part of our understanding of how well non-contact cardiac motion can be utilized for identifying individuals, we investigated the relationship between various radar sensor orientation and identification performance. The hypothesis is that the extracted cardiac feature is insensitive to direction or orientation of the sensor beam. To test this hypothesis, we have collected a set of cardiac motion signals with a certain degree (10~30°) of orientation misalignment. Specifically, multiple radar sensors were used during the collection. One was placed in front of the subject, and others were placed out of alignment. The BAC comparison of each cycle length for different orientation misalignment is shown in FIG. 13. The BAC results for disparate misalignment with 0°, 10°, 20°, 30° are stable as observed from the figure which supports our argument that the extracted cardiac feature is insensitive to direction or orientation of the sensor beam.

Figure 14:
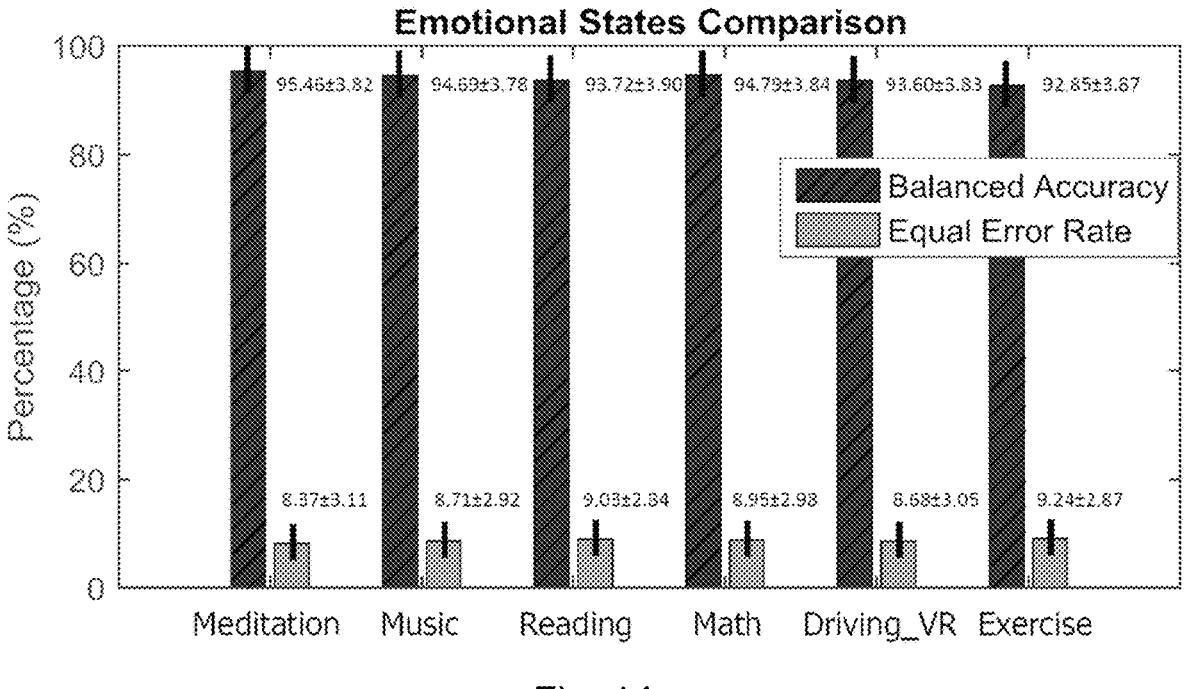
FIG. 14: The comparison among all emotional tasks.

Emotional State: A user's emotional state can change and is unknown to the identification system. The changes in emotional state will affect the cardiac motion (e.g., noise, heartbeat strength/cycle). The hypothesis is that the individualized features in cardiac motion are invariant to the user's emotional state. Research in heart-based biometrics have demonstrated promising results for this hypothesis. To prove the usability and stability of Cardiac Scan under an unknown emotional state, we have conducted a set of experiments examining subjects in different emotional states. We have designated a special protocol to collect cardiac motion signals from low stress to high stress conditions. Specifically, selected subjects will perform two different task groups before collecting the data. The low stress tasks were meditation and listening to peaceful music. The high stress tasks were reading aloud, mathematical manipulation, driving in virtual reality, and intensive exercise. The BAC and EER comparison among all emotional tasks are shown in FIG. 14. The dark gray bars with texture represent BAC and light gray bars represent EER. The BAC and EER exhibit consistent performance across six different activities, including low stress and high stress conditions, which verifies that the emotional state will not impact the system performance.

Figure 15:
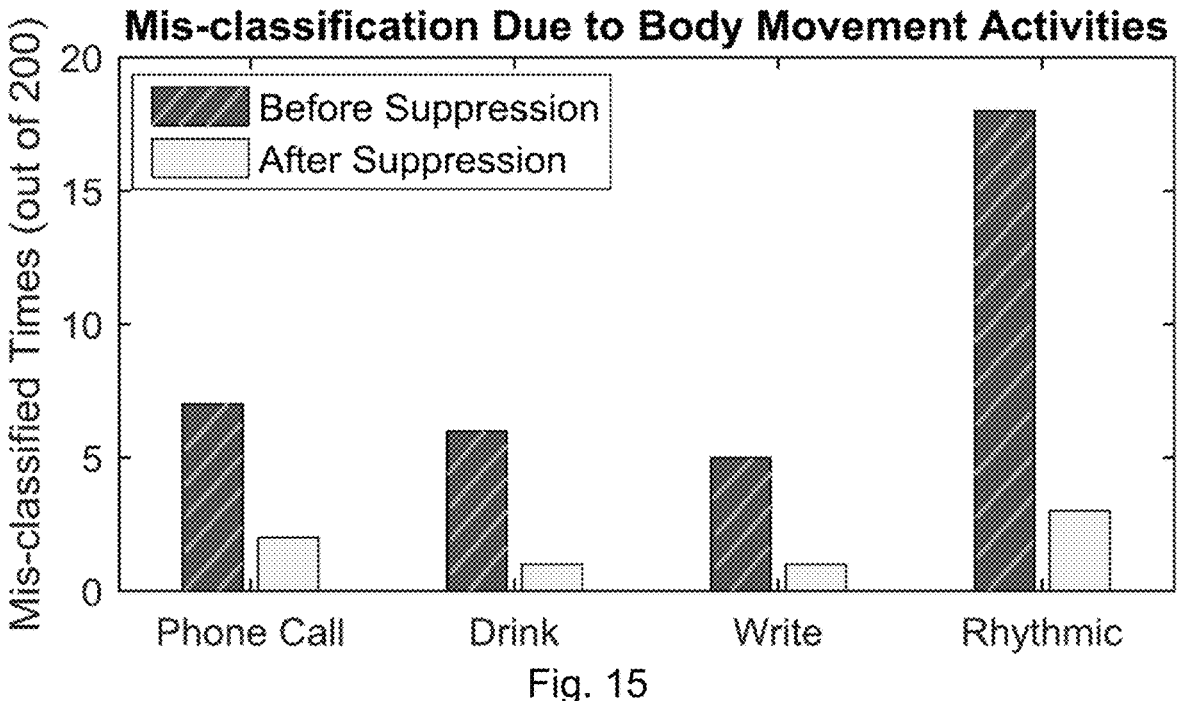
FIG. 15: Body movement suppression before and after.

Subject in Motion: Body movement may result in large perturbations to the output DC offset, and thus confuse the radar demodulation algorithm or even saturate the baseband circuit as described in detail above. In this case, the recognition accuracy may be compromised, thus, the present user will experience logging out of the system. We investigated random movements in four activities ranging from tiny to large-range motions, including writing, drinking water, making phone calls, and one rhythmical movement when listening to music, to show the impact of body movement to the system performance. Twenty subjects participated in the experiment and each one performed all four body movement activities 10 times, a total of 200 trials for each activity are performed. Two radars are deployed in the front and at the back of the human body, and the measurement has to be performed simultaneously from both sides to cancel out the random frequency drift. With the current system setting, we evaluated how many times the authentic user is misclassified as an unauthorized user before and after the body movement suppression approach described above was applied. The comparison results are shown in FIG. 15. Before body movement suppression, the misclassified occurrence was 7 for making a phone call, 6 for drinking water, 5 for writing, and 18 for rhythmic movement. The rhythmic movement was more readily misclassified because it is periodic to some extent. The corresponding results after suppression were reduced to 2 for making a phone call, 1 for drinking water, 1 for writing, and 3 for rhythmic movement.

Continuous Authentication Stability

Besides maintaining a high true positive and true negative rate for authentication, we are particularly interested in low frequency false negative events that misclassify an authentic user as an adversary in continuous authentication. As discussed above, a usable continuous authentication system should always grant an access right to the authentic user as long as he/she is using the system. Otherwise, it is inconvenient even impossible to use the system if the user is being interrupted and asked to login again frequently. We conducted an evaluation on a continuous authentication session with four cardiac cycles setting. Under such configuration, the mean of false negative rate was as low as 0.4%. All 78 subjects participated in this evaluation and each session for each user lasts 40 minutes. Specifically, subject in turn acted as the user to login to the system and sit in front the system, browsing webpages or reading papers, until 40 minutes are reached or be logged out by the continuous authentication system. Not surprisingly, none of the subjects were forced to log out of the system due to a false negative, which is attributed to our continuous authentication protocol and parameters setting to maintain a satisfactory usability as described above.

Longitudinal Study

Figure 16:
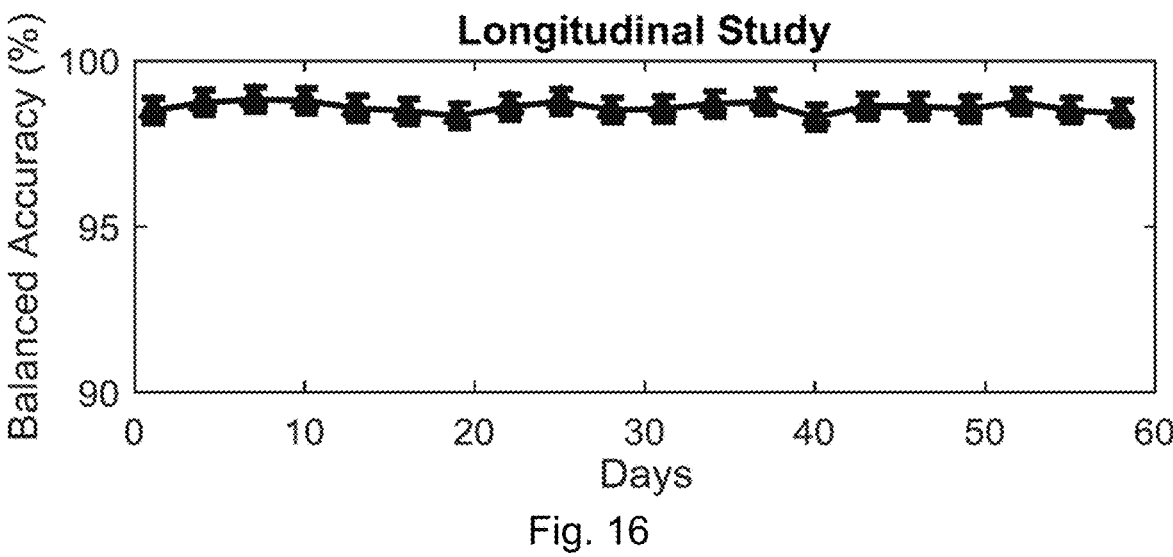
FIG. 16: The 2-month longitudinal BAC performance.

It is important to prove the permanence of biometrics. The permanence of heart-based biometrics was discussed in early experiments in many short-term studies. In addition, each cardiac motion is independent, which means a prior result has no impact on the current result, so subsequent sessions study in short-term periods is not necessary. However, there are currently no longitudinal studies that establish this long-term persistence in any heart-based biometrics. Our generated dataset has included multiple sessions as part of a longitudinal approach to establish a baseline comparison of long-term persistence. 40 subjects (22 males and 18 females) participated in the longitudinal study lasting two months. Particularly, this study has two phases: enrollment phase and authentication phase. In the enrollment phase, training data were collected for each subject at the first day of this longitudinal study. Each subject finishes 20 trials in data collection events with the duration of each trial set as eight seconds. After that, the long-term authentication phase is carried out in the following two months. Each subject performed 20 authentication trials and each authentication duration is four seconds in this study. The BAC measurement is depicted in FIG. 16. In the 60-day duration, mean values of BAC measurement are between 98% and 99%, STDs are between 0.37 and 0.39. We concluded the BAC has no significant performance decreasing or ascending tendency, which demonstrates cardiac motion is robust against time change.

Vulnerability Study

We also investigated the vulnerability of Cardiac Scan. Although cardiac motion is invisible and might possess better safety and security than other authentication approaches (e.g., PIN, fingerprint), it could become fallible under direct or spoofing attacks. One immediate attack approach is the presentation of human characteristics to the acquisition device, including different living traits (i.e., zero-effort impostor attempts that try to take advantage of the false acceptance rate (FAR) of biometric systems).

Replay Attack

One risk of using biometrics is the danger that the biometric token can be intercepted and replayed by an unauthorized party. Compared to visual-based still biomet-

Figure 17:
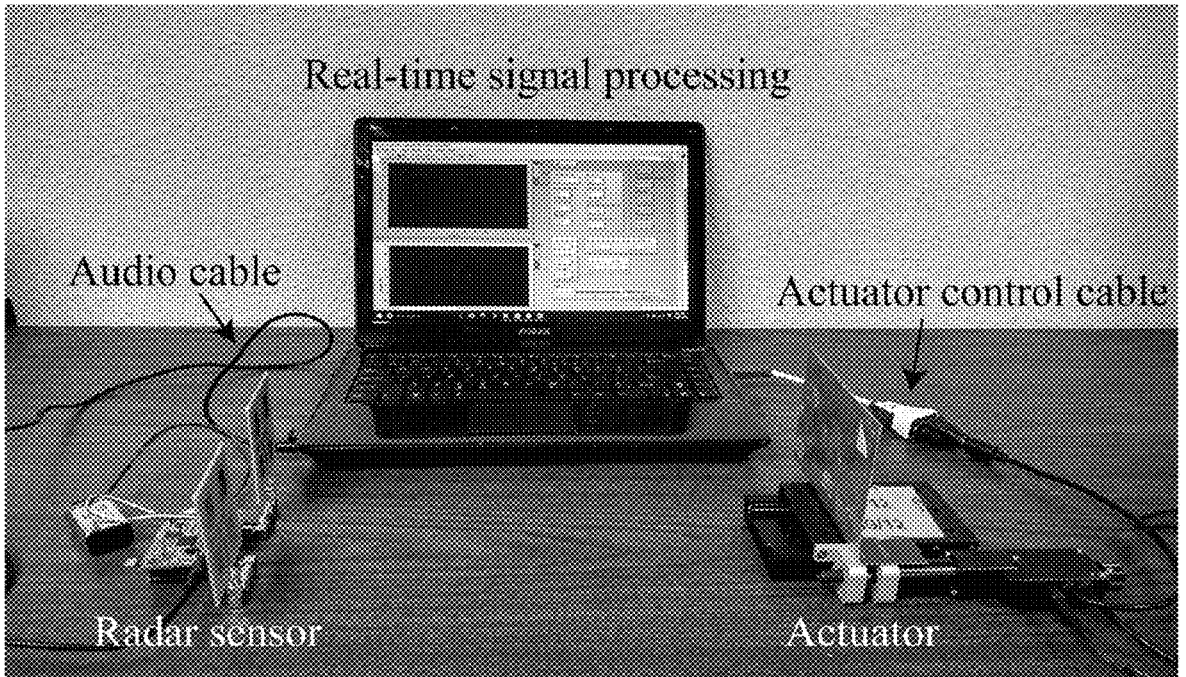
FIG. 17: A linear actuator imitates cardiac motion.

23 rics (face/fingerprint/iris), the cardiac signal is more complex and dynamic to fake or replicate. However, there is still a chance to compromise cardiac signal under some extreme scenarios. Recently, Eberz et al. used a hardware-based arbitrary waveform generator (AWG) and a sound card based AWG software to encode and emulate a set of pulse signals for attacking heart-based biometrics on the Nymi band. Attackers might also hack into the database and obtain cardiac motion patterns or engineer the same cardiac motion sensing device to extract a user's cardiac signals. This work is to prove the possibility of a replay attack on Cardiac Scan if a legitimate user's cardiac signals are obtained by attackers. Our team has investigated the method of synthesizing cardiac motion and developed a programmable actuator to imitate the cardiac motion. As shown in FIG. 17, a linear actuator (ZABER TNA08A50) and a linear translational stage (i.e., ZABER TSB28-1) were placed 30 cm from the cardiac motion-sensing device. The actuator was programmed to perform a harmonic back-and-forth motion toward the radar for mimicking cardiac motion patterns.

Anti-Spoofing: Liveness Artifacts

Our team has also investigated a set of anti-spoofing approaches against a replay attack. The general idea of anti-spoofing is liveness detection. Liveness detection has been applied to existing biometrics systems by using affiliated living traits of humans by considering that it is relatively challenging to emulate multiple human traits at the same time during one spoofing attack section. For example. Pan et al. proposed a method to extract liveness information through eye blinks in face recognition. Wei et al. detected counterfeit iris through texture analysis. In the present work, we have exploited the uniqueness of living traits in human cardiac motion to defend the above adversarial model. Specifically, we have tackled this challenge from two dimensions: hardware-based and software-based approaches. First, in some embodiments, we integrated assisted sensors in Cardiac Scan so that we can leverage additional information from these sensors to examine the legitimacy of subjects and capture the characteristics of multi-dimensional cardiac motions for liveness simultaneously. Specifically, as discussed above, the system employed multi-channel radars for noise reduction. Since the linear actuator only moves in rectilinear directions, the direction of arrival (DoA) measurements with the linear actuator on these radars are different from DoA measured with real cardiac motion. Second, we have investigated software-based approaches. Because the sensor data from a live subject inevitably include vital sign(s) (e.g., respiration) and other motion artifacts (e.g., body sway). These artifacts are not stored in the system database as credentials, so they are unable to be replicated and emulated for attack. Utilizing detection of such vital sign(s) and motion artifacts, liveness detection may be conducted against a replay attack. We programmed the actuator working with different moving amplitudes and frequencies to imitate cardiac motions of 12 subjects. All replay attacks were rejected by our liveness detection method.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

24

What is claimed is:

1. A method for authenticating an individual using a motion of a physiological structure of the individual, comprising:

transmitting, by a radar sensor, a first radiofrequency ("RF") signal towards the physiological structure of the individual;

receiving, by the radar sensor, a first RF return signal corresponding to the transmitted first RF signal interacting with the physical structure of the individual;

processing, by a processor, the first RF signal and first RF return signal to obtain a motion signal of the physical structure;

determining, by the processor, one or more values for each fiducial point of a set of pre-determined fiducial points in the motion signal, wherein the set of pre-determined fiducial points corresponds to physical movements of the physiological structure; and wherein the set of pre-determined fiducial points of the motion signal comprises one or more of a cycle start (ST), a first maximum amplitude of movement (AFP), a second maximum amplitude of movement (VFP), a local minimum amplitude between AFP and VFP (ASP), and a cycle end (ED);

authenticating, by the processor, the individual based on the one or more values for each fiducial point of the set of pre-determined fiducial points.

2. The method of claim 1, wherein the physiological structure is a heart of the individual.

3. The method of claim 1, wherein the receiving the first RF return signal comprises sampling, by the processor, the first RF return signal at a sampling frequency.

4. The method of claim 1, wherein the one or more values for each fiducial point correspond to an amplitude difference and/or a time difference between one or more of ST and AFP, AFP and ASP, ASP and VFP, and VFP and ED.

5. The method of claim 1, wherein the authenticating the individual further comprises calculating, by the processor, derivative values based on the one or more values of the set of pre-determined fiducial points.

6. The method of claim 1, wherein the processing the first RF signal and the first RF return signal further comprises noise reduction and applying phase demodulation.

7. The method of claim 6, wherein the noise reduction includes applying a Butterworth bandpass filter and/or applying a normalized least mean square adaptive filter to the first RF return signal.

8. The method of claim 6, wherein the phase demodulation includes:

phase demodulating the first RF return signal using an arctangent demodulation;

computing a derivative to the arctangent-demodulated phase information as w (t) according to:

$$\omega(t) = \frac{d}{d_t}\left[\arctan\frac{Q(t)}{I(t)}\right] = \frac{I(t)\dot{Q}(t) - \dot{I}(t)Q(t)}{I(t)^2 + Q(t)^2},$$

where $\omega(t)$ is related to the velocity function of the cardiac motion, and $\dot{Q}(t)$ and $\dot{I}(t)$ denote the time derivative of Q(t) and I(t), respectively;

integrating $\omega(t)$ to obtain signal phase $\Phi_\theta[n]$; and obtaining motion x[n] based on the signal phase $\Phi_\theta[n]$.

9. The method of claim 6, wherein the phase demodulation includes:

obtaining DC component offsets of the in-phase and quadrature channels of the first RF return signal; and phase demodulating the first RF return signal using the DC component offsets to obtain a displacement signal x(t).

* * * * *